(12) United States Patent
Bernstein et al.

(10) Patent No.: US 9,714,424 B1
(45) Date of Patent: Jul. 25, 2017

(54) RNAI INHIBITION OF USP10 TO TREAT OCULAR DISORDERS

(71) Applicants: Audrey Bernstein, Jersey City, NJ (US); Stephanie Gillespie, New York, NY (US)

(72) Inventors: Audrey Bernstein, Jersey City, NJ (US); Stephanie Gillespie, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 14/969,865

(22) Filed: Dec. 15, 2015

Related U.S. Application Data

(60) Provisional application No. 62/092,552, filed on Dec. 16, 2014, provisional application No. 62/249,026, filed on Oct. 30, 2015.

(51) Int. Cl.
*C12N 15/113* (2010.01)
*G01N 33/50* (2006.01)

(52) U.S. Cl.
CPC ..... *C12N 15/1137* (2013.01); *G01N 33/5023* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2005/0255487 A1* | 11/2005 | Khvorova | ............ | A61K 31/713 435/6.11 |
| 2012/0171192 A1* | 7/2012 | Lou | ................... | A61K 31/7105 424/94.63 |

OTHER PUBLICATIONS

Asano, Y., H. Ihn, M. Jinnin, Y. Mimura, and K. Tamaki. "Involvement of alphavbeta5 integrin in the establishment of autocrine TGF-beta signaling in dermal fibroblasts derived from localized scleroderma." J Invest Dermatol. 126:1761-1769, 2006.

Bernstein, A.M., S.S. Twining, D.J. Warejcka, E. Tall, and S.K. Masur. 2007. "Urokinase receptor cleavage: a crucial step in fibroblast-to-myofibroblast differentiation." Mol Biol Cell. 18:2716-2727.

Bomberger, J.M., R.L. Barnaby, and B.A. Stanton. 2009. "The deubiquitinating enzyme USP10 regulates the post-endocytic sorting of cystic fibrosis transmembrane conductance regulator in airway epithelial cells." J Biol Chem. 284:18778-18789.

Carrington, L.M., J. Albon, I. Anderson, C. Kamma, and M. Boulton. 2006. "Differential regulation of key stages in early corneal wound healing by TGF-beta isoforms and their inhibitors." Invest Ophthalmol Vis Sci. 47:1886-1894.

Do Carmo Costa, M., F. Bajanca, A.J. Rodrigues, R.J. Tome, G. Corthals, S. Macedo-Riberio, H.L. Paulson, E. Logarinho, and P. Maciel. 2010. "Ataxin-3 plays role in mouse myogenic differentiation through regulation of integrin subunit levels." PLoS One. 5:e11728.

Henderson, N.C., T.D. Arnold, Y. Katamura, M.M. Giacomini, et. al. 2013. "Targeting of alphav integrin identifies a core molecular pathway that regulates fibrosis in several organs." Nat Med. 19:1617-1624.

Kapp, T.G., F. Rechenmacher, T.R. Sobahi, and H. Kessler. 2013. "Integrin modulators: a patent review." Expert Opin Ther Pat. 23:1273-1295.

Lobert, V.H., A. Brech, N.M. Pedersen, J. Wesche, A. Oppelt, L. Malerod, and H. Stenmark. 2010. "Ubiquitination of alpha 5 beta 1 integrin controls fibroblast migration through lysosomal degradation of fibronectin-integrin complexes." Dev Cell. 19:148-159.

Parapuram, S.K., and W. Hodge. 2014. "The integrin needle in the stromal haystack: emerging role in corneal physiology and pathology." J Cell Commun Signal.

Van De Water, L.S. Varney, and J.J. Tomasek. 2013. "Mechanoregulation of the Myofibroblast in Wound Contraction, Scarring, and Fibrosis: Opportunities for New Therapeutic Intervention." Adv Wound Care (New Rochelle)." 2:122-141.

Wang, L., B.S. Pedroja, E.E. Meyers, A.L Garcia, S.S. Twining, and A.M. Bernstien. 2012. "Degradation of Internalized alphavbeta5 Integrin is Controlled by uPAR Bound uPA: Effect on beta1 Integrin Activity and alpha-SMA Stress Fiber Assembly." PLoS One. 7:e33915.

Wilson, S.E. 2012. "Corneal myofibroblast biology and pathobiology: Generation, persistence, and transparency." Exp Eye Res. 99:78-88.

Wipiff, P.J., and B. Hinz. 2008. "Integrins and the activation of latent transforming growth factor beta1—An intimate relationship." Eur J Cell Biol. 87:601-615.

* cited by examiner

*Primary Examiner* — Richard Schnizer
(74) *Attorney, Agent, or Firm* — Lawrence S. Cohen

(57) ABSTRACT

Reduction of ocular scarring is accomplished from the discovery that silencing of the expression of USP10 in the area of a wound under healing will reduce the accumulation of integrin on the cell's surface and activation of the fibrotic growth factor TGFβ, thereby preventing ocular scarring.

13 Claims, 12 Drawing Sheets

RNAI INHIBITION OF USP10 TO TREAT OCULAR DISORDERS

RELATED APPLICATIONS

This reference to Provisional Application No. 62/092,552 filed on Dec. 16, 2014 is made for the purpose of claiming priority to and the benefit of said provisional application the entire content of which is incorporated herein by reference. This reference to Provisional Application No. 62/249,026 filed on Oct. 30, 2015 is made for the purpose of claiming priority to and the benefit of said provisional application the entire content of which is incorporated herein by reference.

SEQUENCE LISTING

The sequence listing is set out in the Appendix A attached to and incorporated by reference herein. The same sequence listing in an ASCII text file has been filed as 14-130-seqlist.txt.

BACKGROUND

The present invention relates to the field of ocular disorders.

In the eye, scarring obstructs vision. Worldwide, ocular scarring is the leading cause of monocular blindness. Initial wound healing responses prevent infection but subsequent tissue repair must result in regenerative healing to prevent the development of blinding scar tissue in the eye.

Glaucoma is a disease where extracellular matrix accumulates in the trabecular meshwork, decreasing aqueous outflow and increasing pressure in the eye. Increased integrin-mediated cell adhesion of trabecular meshwork cells contributes to this transformation.

The surgery to relieve the pressure that is associated with Glaucoma is a trabeculectomy surgery. The "bleb" or flap that is made to relieve pressure often heals with a scar, reversing the benefit of the surgery. Currently mitomycin C treatment is used to halt all cell proliferation after surgery in an effort to stop this scarring outcome. This treatment is unpredictable and has safety concerns. The cells that proliferate and differentiation are called tenon fibroblasts.

Another major point of fibrotic scarring in the eye is in the layer of epithelial cells called Retinal Pigmented Epithelial cells (RPE). The RPE layer of cells is adjacent to the retina. They are critical to vision and the correct functioning of the retina. The migration and proliferation of the RPE cells is called epithelial to mesenchymal transition (EMT), which leads to the development of fibrotic RPE myofibroblasts and a thick disorganized extracellular matrix covering the retina. Major diseases that either derive from or end with fibrotic outcomes in the RPE layer are age-related macular degeneration, diabetic retinopathy, and proliferative vitreoretinopathy.

Age-related macular degeneration (AMD) is the loss of photoreceptors in the central retina. Degeneration of the macula is associated with abnormal deposition of extracellular matrix called Drusen in the membrane between the RPE and the vascular choroid inducing a fibrovascular subretinal membrane leading to retinal scarring.

Proliferative Diabetic Retinopathy (PDR) is the more advanced stage of Diabetic Retinopathy, a disorder that develops in diabetic patients typically after a decade with the disease. An over accumulation of sugars damages the blood vessels in the retina. PDR is characterized by neovascularization into the retina. New aberrant blood vessels leak blood and growth factors that induce EMT ending in the development of fibrotic RPE myofibroblasts and a thick disorganized extracellular matrix covering the retina. This leads to retinal detachment.

Proliferative vitreoretinopathy (PVR) occurs after mechanical retinal detachment, fluid from the vitreous humor enters a retinal hole. During this process the RPE comes in contact with vitreous cytokines that induces EMT (fibrotic epithelial-derived myofibroblasts), which secrete disorganized extracellular matrix and fibrotic cytokines. This leads to scarring of the retina.

SUMMARY

Scar tissue results from the persistence of myofibroblasts in a healing wound. Persistent myofibroblasts are overly adhesive cells that self-activate the fibrotic growth factor, TGFβ, leading to the overproduction of disorganized extracellular matrix, excessive contraction, and scarring. Global neutralization of TGFβ reduces myofibroblast differentiation but also prevents cell repopulation and wound closure. Thus, innovative approaches that directly target the myofibroblast population in a fibrotic tissue are required.

The present invention is a method of reducing ocular scarring in ocular wound healing and other ocular disorders. The invention derives from the discovery that the protein expression of the de-ubiquitinase (DUB) USP10 is increased after wounding and that USP10 promotes a scarring outcome by removing the post-translational modification referred to as ubiquitin from the β5 subunit of integrin αvβ5 protein. This deubiquitinase activity of USP10 reduces the degradation of integrin αvβ5 leading to its accumulation on the cell surface with two subsequent effects: a) overly adherent and persistent myofibroblasts as is evidenced by the organization of α-smooth muscle actin stress fibers and b) the activation of the fibrotic growth factor, TGFβ.

These processes promote fibrotic healing instead of the desired regenerative healing. Therefore it is the invention derived from these discoveries, to reduce the DUB USP10 protein or activity and therefore its undesirable consequences. That method is to reduce USP10 mRNA and protein expression by treatment with an interfering RNA, as more detailed hereafter.

The present invention is directed to interfering RNAs that targets USP10 mRNA and thereby interfere with USP10 mRNA expression. The interfering RNAs of the invention are useful for treating USP10-related ocular scarring as a result of corneal wounds or corneal disease, glaucoma, bleb scarring after trabeculectomy surgery, age-related macular degeneration, diabetic retinopathy, and proliferative vitreoretinopathy.

An embodiment of the present invention provides a method of attenuating expression of USP10 mRNA in an eye of a patient. The method comprises administering to the eye in an area undergoing a healing process of a therapeutically effective amount of interfering RNA to wholly or substantially interfere with USP10 mRNA expression.

The siRNA is applied with a clinically acceptable carrier. Exemplary embodiments of the invention are double-stranded (ds) siRNA or single-stranded (ss) siRNA at a length of 19 to 49 nucleotides.

The double stranded siRNA comprises a sense nucleotide sequence, an antisense nucleotide sequence and a region of at least near-perfect contiguous complementarity of at least 19 nucleotides. Further, the antisense sequence hybridizes under physiological conditions to a portion of mRNA corresponding to SEQ ID NO: 1 (the sense strand sequence of DNA for human USP10, GenBank reference no. NM_001272075.1), and has a region of at least near-perfect contiguous complementarity of at least 19 nucleotides with the hybridizing portion of mRNA corresponding to SEQ ID NO: 1. The administration of such a composition (SEQ ID NO: 2-7) attenuates the expression of USP10 mRNA of the eye of the subject.

The cornea has a stratified epithelium with an underlying basement membrane. 90% the depth of the cornea is the corneal stroma containing quiescent keratocytes embedded in a perfectly organized transparent lattice of collagen and proteoglygans. The corneal endothelium is a monolayer of cells that controls the flow of solutes into and out of the cornea. The function of the cornea in the eye is to focus incoming light onto the lens and the retina and for the protection of the eye.

Figure 2:
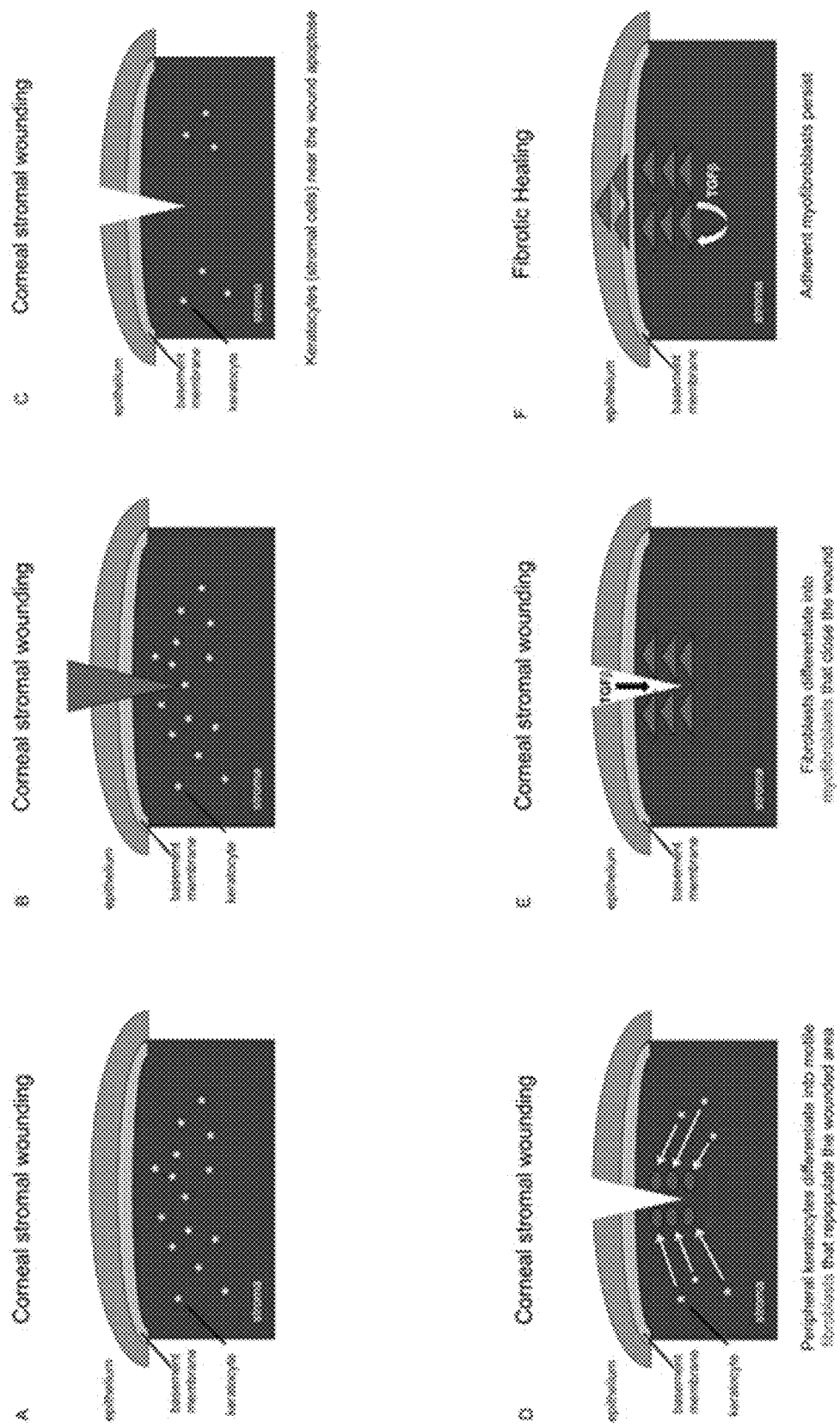

FIG. 2 depicts how wounding in the cornea generates a scar after a penetrating wound.

A-F) Wounding through the epithelium and underlying basement membrane induces fibrotic scarring in the anterior stroma. The normally quiescent keratocytes differentiate into fibroblasts that migrate into the wound site. Fibroblasts differentiate into myofibroblasts that function to close the wound, however, the persistence of myofibroblasts in a wound results in scarring in the cornea and in all tissues in the body. It is demonstrated in this Description that reducing the number of myofibroblasts after wounding not only prevents fibrotic scarring but also induces a regenerative healing program. The cornea is an excellent model system to study agents that promote regenerative healing because of the accessibility of human tissue and the ability to perform organ culture studies.

Figure 3:
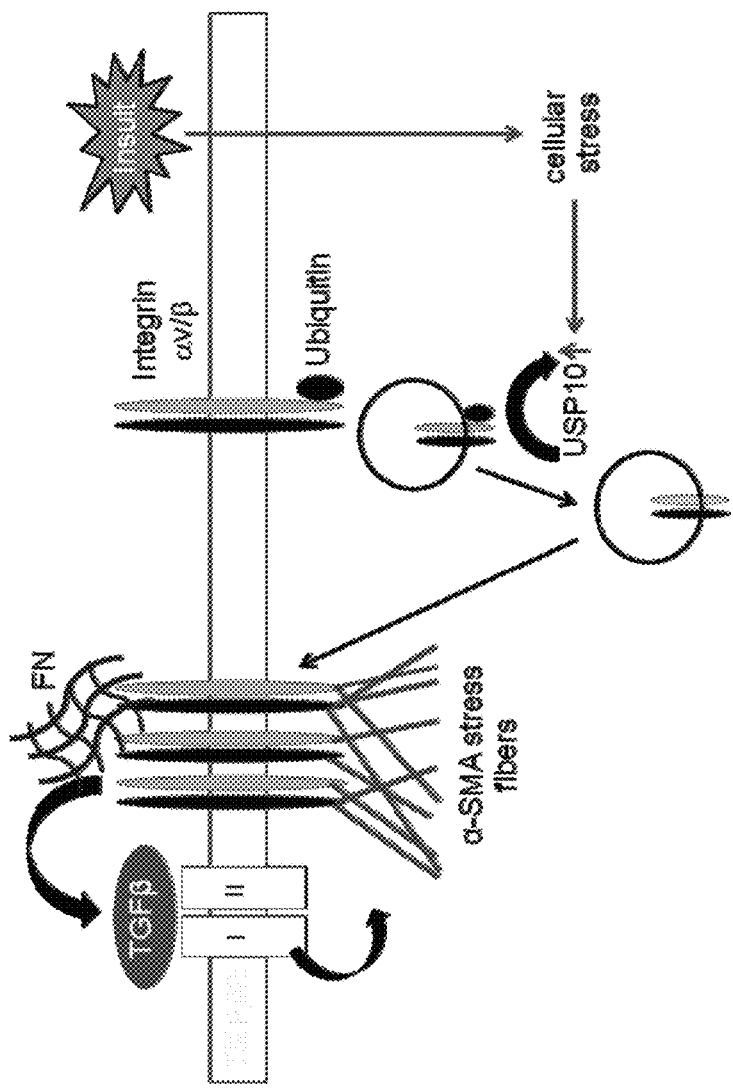

FIG. 3 is an overview of the demonstrated mechanism of how the induction of USP10 protein after wounding generates persistent myofibroblasts leading to fibrotic scarring.

Figure 4:
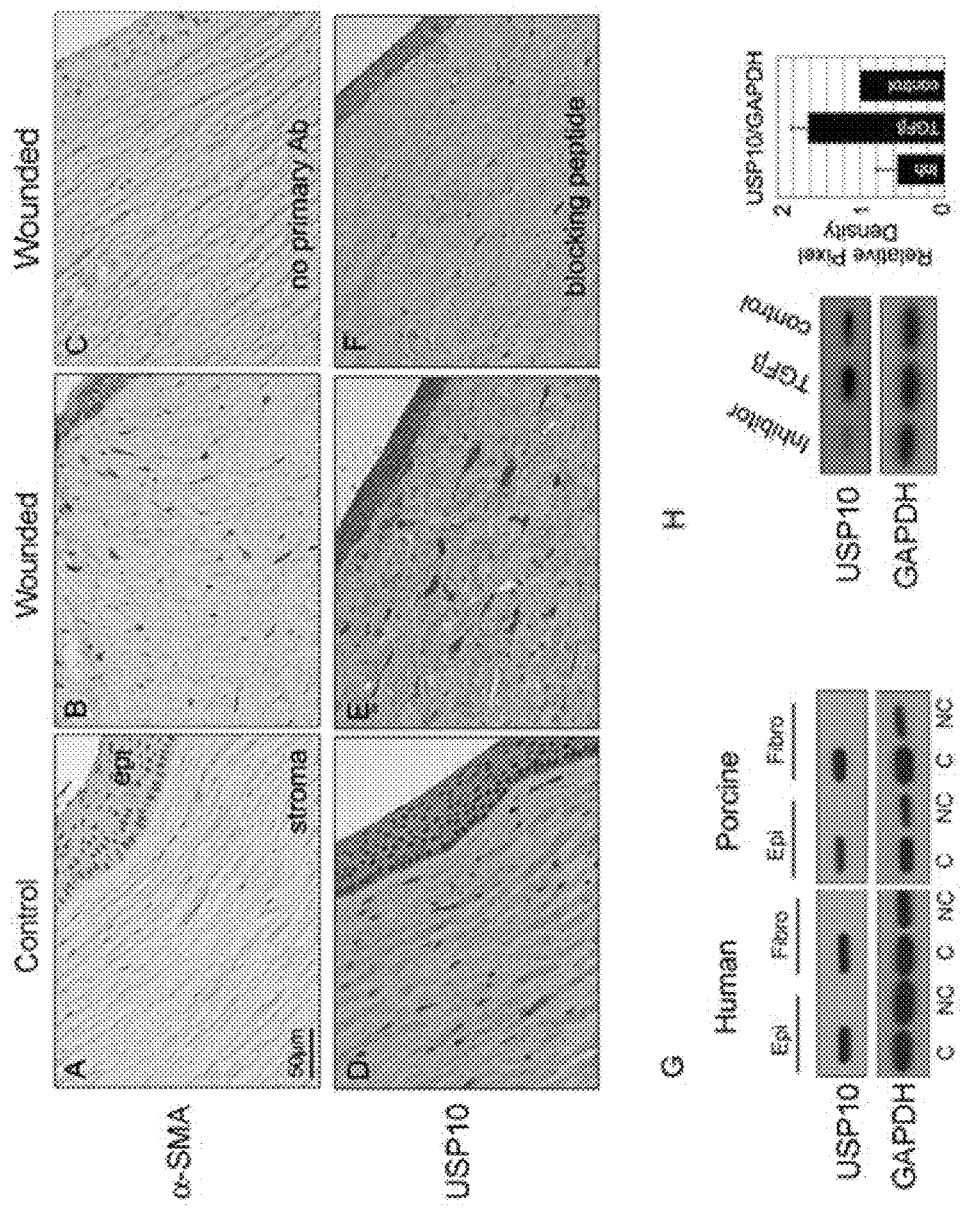
Figure 5:
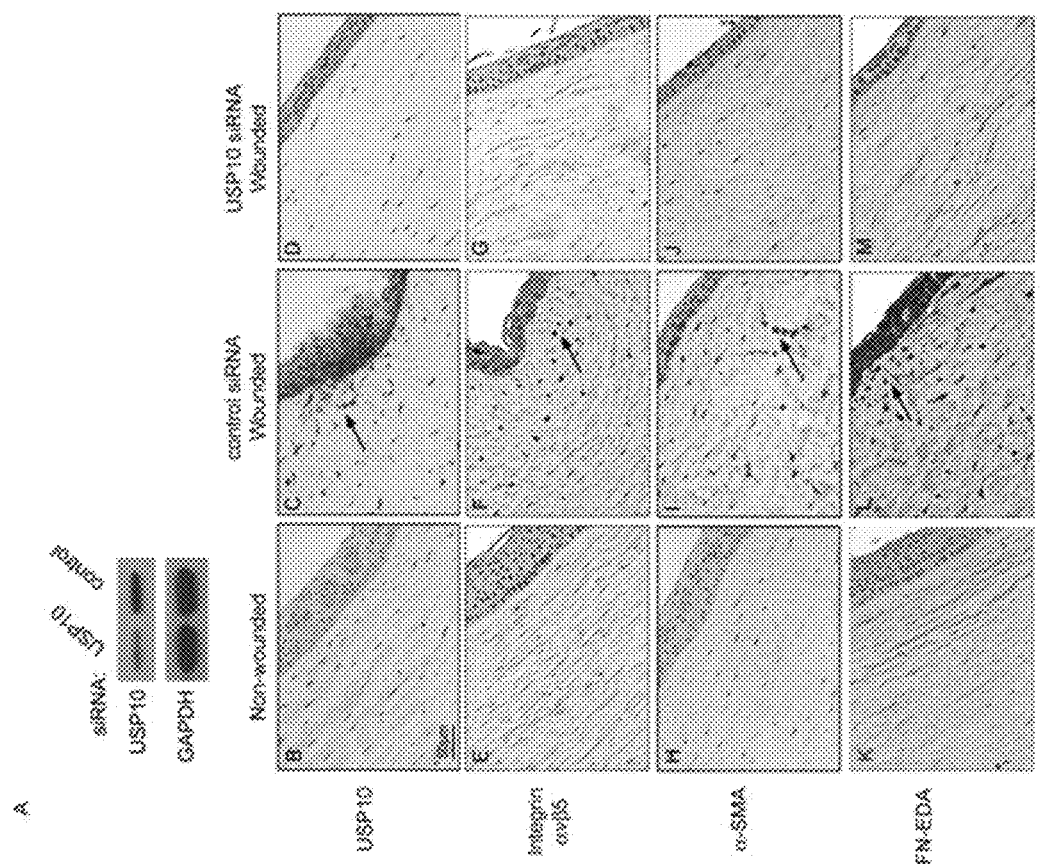
Figure 7:
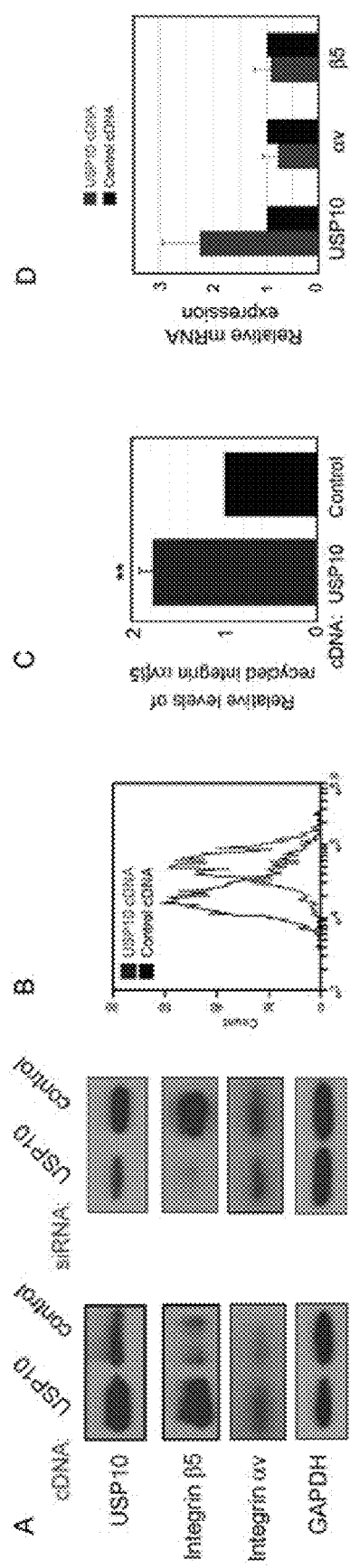
Figure 8:
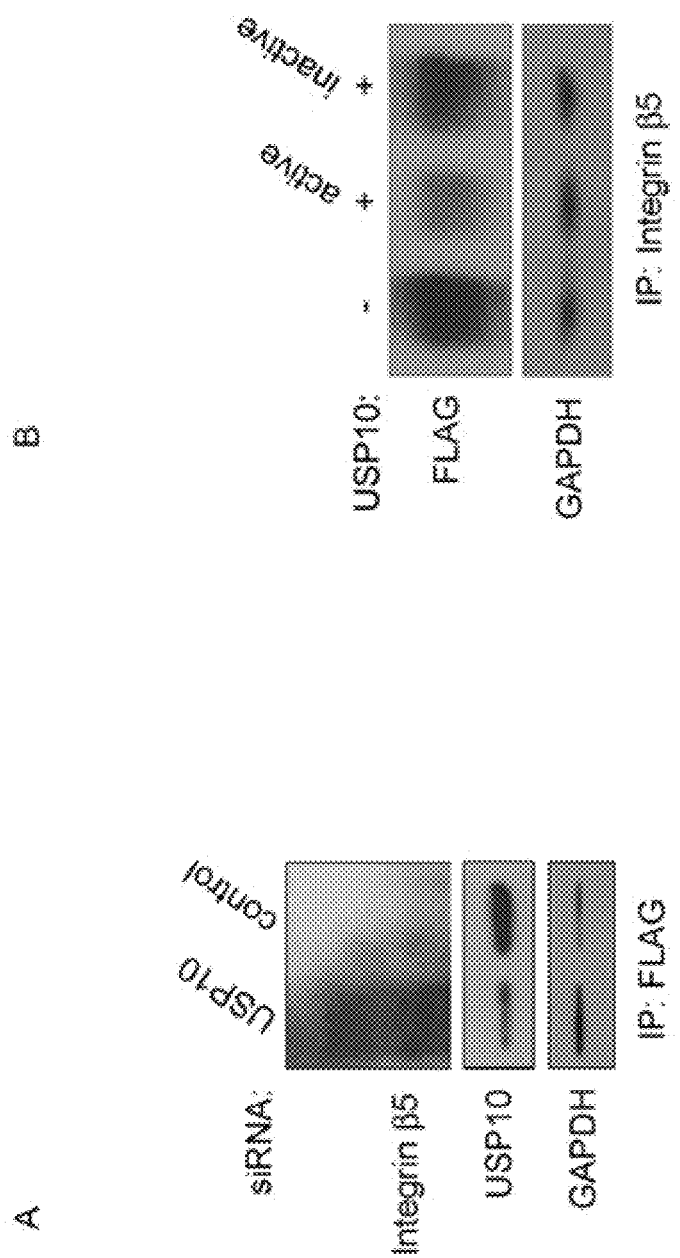
Figure 9:
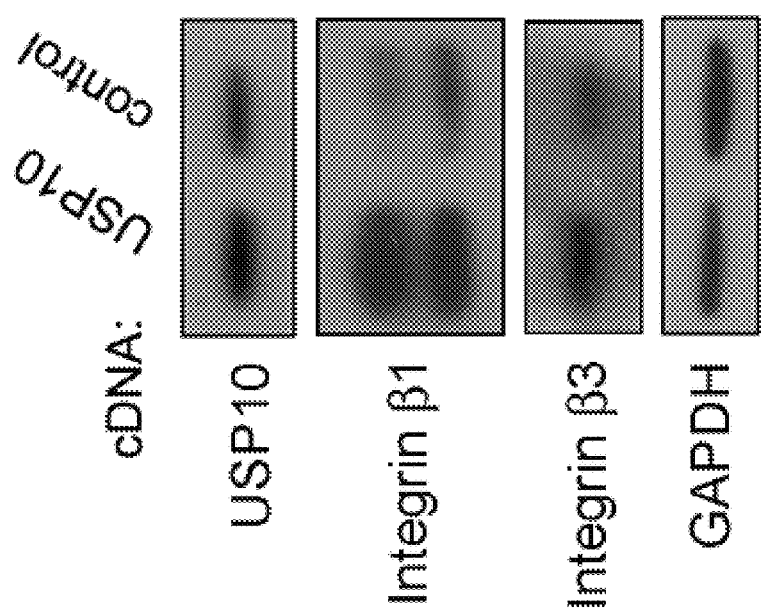
Figure 10:
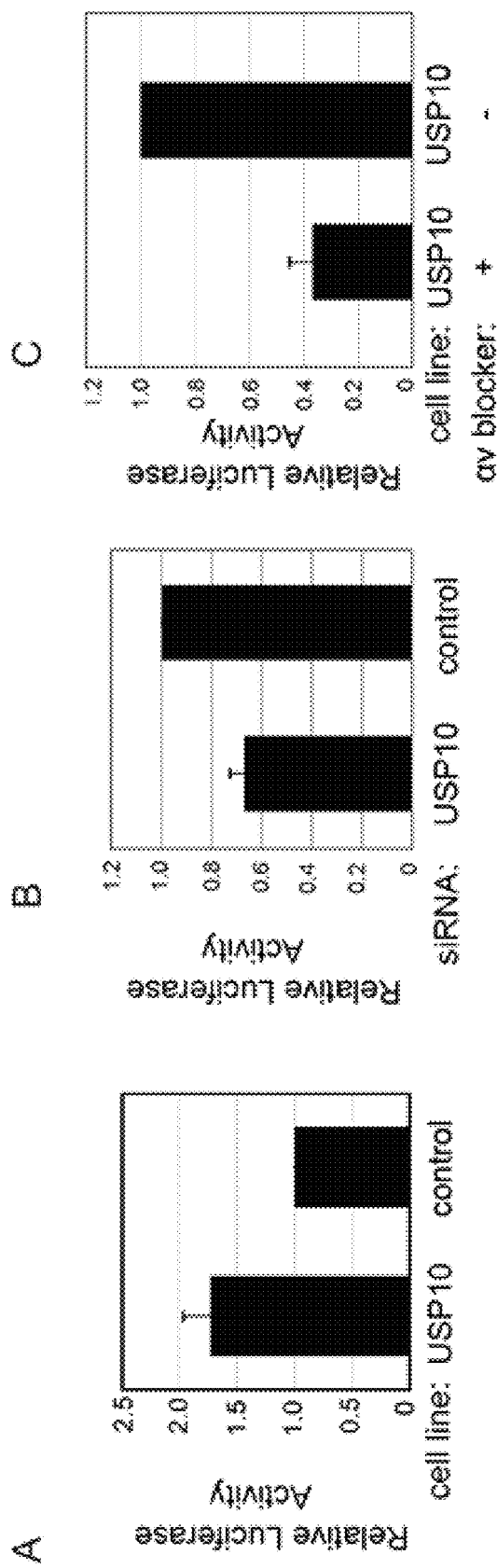
Figure 11:
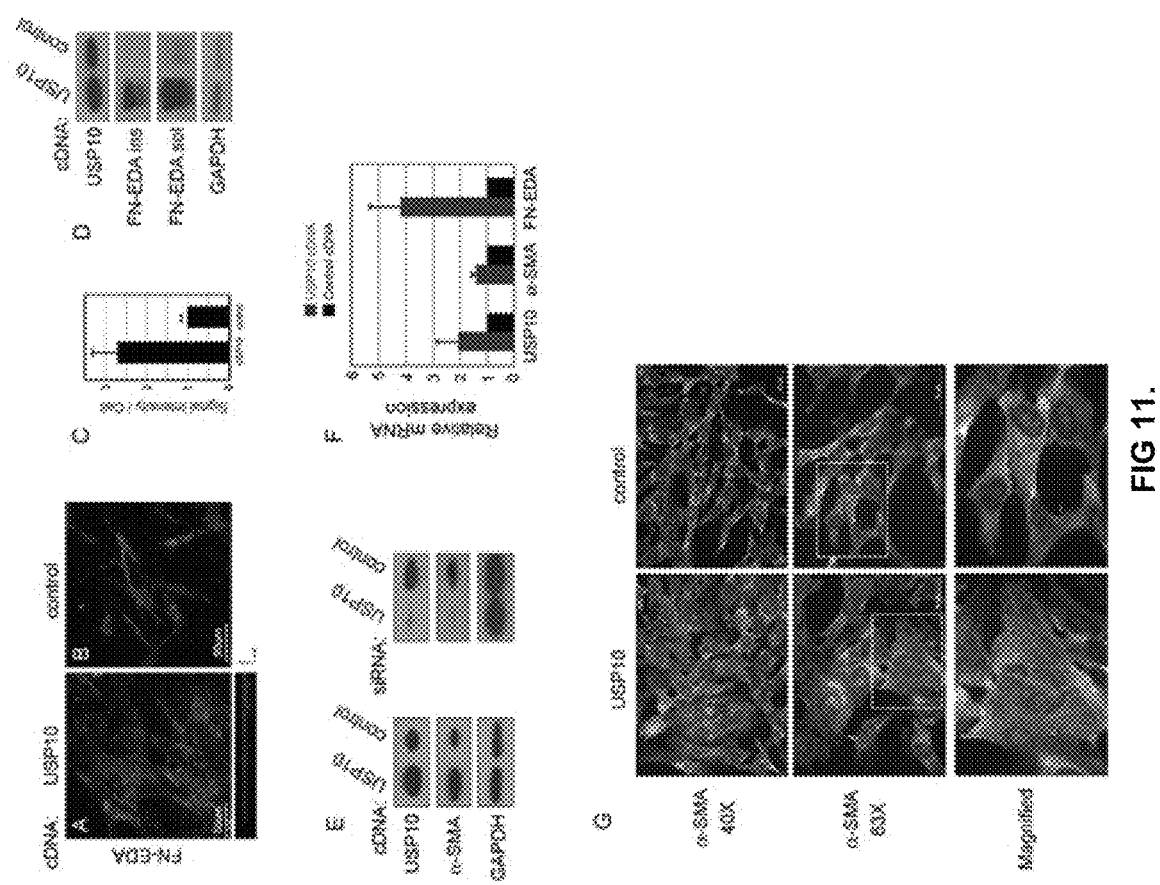

These data were generated in human corneal stromal fibroblast cell culture and in porcine corneal organ culture. We demonstrate that:

a) after wounding, TGFβ that is secreted from local sources (in the cornea, the epithelium) induces the protein expression of the de-ubiquitinase (DUB), USP10 (FIG. 4). Whereas, the reduction of USP10 gene expression with siRNA to USP10 after corneal wounding prevents the expression of fibrotic markers and promotes regenerative healing (FIG. 5).

b) USP10 post-translationally regulates integrin αvβ5 by removing ubiquitin. This action promotes the recycling of integrin αvβ5 back to the cell surface where it accumulates instead of being degraded inside the cell (FIGS. 7 and 8). USP10 also promotes the accumulation of the other alpha v integrins, αvβ3 and αvβ1 (FIG. 9).

c) USP10 over-expression induces TGFβ activity (because of the accumulation of integrin αv integrins on the cells surface, FIG. 10).

d) Increased cell-surface integrin-mediated adhesion and TGFβ activity induces the expression and organization of FN-EDA and α-SMA containing stress fibers, key fibrotic markers (FIG. 11).

FIG. 4 demonstrates that α-SMA (fibrotic marker) and USP10 are generated in corneal organ culture after wounding.

Porcine corneas with scleral rims were mounted on an agarose/collagen base without wounding (control corneas) or after wounding through the anterior stroma with a trephine (wounded corneas). A-H immunostaining of paraffin embedded corneal slices comparing control to 2 weeks post-wounding. Compared to control fibrotic markers increased in the anterior stroma after wounding: (A, B) α-SMA 2.9-fold+/−0.8 *p<0.005, (C) No primary antibody control, (D, E) USP10 2.5-fold+/−0.8 p<0.01, and F) Pre-incubation with a USP10 blocking peptide reduced immunostaining. Bar=50 um. (G) Western blot of human and porcine primary epithelial cells (Epi) and stromal cells (Fibro). (C, Cultured cells; NC, non-cultured cells, (lysed immediately after isolation) demonstrates that culturing cells in serum-containing media (a model for wounding in culture) induces USP10 protein expression. (H) HCFs were treated with 1 ng/ml TGFβ1, the TGFβ inhibitor (SB431542), or SSFM alone (control). N=3-5, demonstrating that USP10 protein expression is induced at least in part by TGFβ.

FIG. 5 Silencing USP10 ex-vivo decreases the fibrotic wound healing response.

A) Primary porcine corneal fibroblasts were transfected with human USP10 or control siRNA and Western blotted for USP10. B-M) Porcine corneas were cultured as in FIG. 4 and either unwounded (control) or wounded and treated with control or USP10 siRNA. B-M) After addition of USP10 siRNA, USP10 is reduced 2-fold+/−0.6 p<0.01; integrin αvβ5 3.7-fold+/−1.2 p<0.01; α-SMA 2.2-fold+/−0.6 *p<0.005; and FN-EDA 3.3-fold+/−1.2 p<0.01. Immunostaining of wounded corneas treated with USP10 siRNA were equal to non-wounded controls in all experiments; comparisons of means between control and USP10 knockdown were non-significant. Bar=50 uM. N=3-5. Statistical significance calculated by one-way ANOVA with Bonferroni's test.

Figure 6:
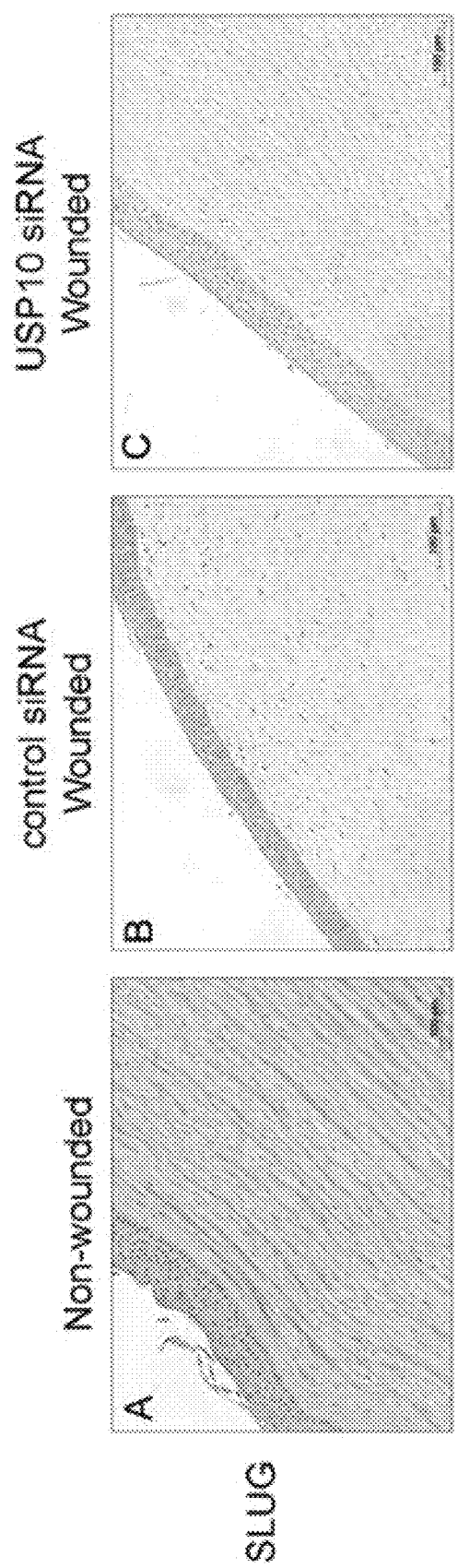

FIG. 6 SLUG is expressed in the corneal epithelium after wounding.

Porcine corneas were cultured as in FIG. 4 and were either A) unwounded (control) or B) wounded and treated with control siRNA or C) wounded and treated with USP10 siRNA. Sections were immunostained with anti-SLUG antibody. After treatment of the wounded cornea with USP10 siRNA, SLUG staining decreased 4.4-fold+/−1.3 *p<0.05 compared to control siRNA. SLUG is a marker for EMT (epithelial mesenchymal transition). These data demonstrate that corneal wounding induces EMT (differentiation of epithelial cells into myofibroblasts in the regrown epithelium) and that siRNA to USP10 significantly reduces this transition.

FIG. 7 demonstrates that USP10 regulates integrin αvβ5 protein levels and cell-surface protein expression but not gene expression.

A) HCFs were transfected with USP10-cDNA or control vector; USP10 siRNA or control siRNA. Cell lysates were Western blotted for USP10, integrin β5, αv, and GAPDH. USP10 overexpression increases β5, (3.3 fold+/−0.4) and αv (3.3+/−1.0). USP10 silencing decreases β5 (90%+/−5%) and αv (88%+/−28%) (Exposure times vary between cDNA and siRNA experiments and thus band densities between the two cannot be compared).

B) Flow cytometry for cell surface integrin αvβ5, (shown is a representative experiment), average increase—1.62 fold+/−0.4.

C) USP10 over-expression increases integrin αvβ5 recycling to the cell surface. (70% increase+/−9%, **p<0.01, N=5.

D) qRT-PCR for USP10, αv and β5 after USP10 overexpression compared to control, (USP10 2.2-fold increase+/−0.3 *p<0.05, αv and β5 10% non-significant decrease). Together these data demonstrate that USP10 regulates integrin αvβ5 post-translationally. N=3-5.

FIG. 8 demonstrates that USP10 removes ubiquitin from integrin β5 (that USP10 is a DUB for the subunit integrin β5, of αvβ5).

A cell line that over-expresses ubiquitin linked to a FLAG tag was created in htert immortalized fibroblasts (htert-ubiquitin cells).

A) Htert ubiquitin-FLAG cells were transfected with USP10 siRNA or control siRNA in the presence of 10 uM chloroquin. Lysates were immunoprecipitated with anti-FLAG beads. Eluted proteins were Western blotted for integrin I35, USP10 and GAPDH. Ubiquitinated β5 is increased 1.9-fold+/−0.5 after treatment with USP10 siRNA compared to control siRNA.

B) Htert-ubiquitin-FLAG cell lysates were immunoprecipitated with antibody to integrin αvβ5. The IP was either not treated or treated with 20 nM active or inactivated recombinant USP10 protein. Eluted proteins were Western blotted for FLAG. After addition of recombinant USP10, I35 ubiquitination is decreased by 2.6-fold+/−0.9. N=3.

FIG. 9 demonstrates that integrins αvβ3 and αvβ1 are regulated by USP10 protein expression. HCFs were transfected with USP10-cDNA or control vector. Cell lysates were Western blotted for USP10, integrin β3, β1, and GAPDH. USP10 overexpression (USP10 cDNA) increases Integrin β1 (3.9+/−1.1) and Integrin β3 (2.0+/−0.1).

FIG. 10 demonstrates that USP10 induces TGFβ activity.

The intracellular binding of the transcription factor, SMAD to its DNA binding element is induced by the extracellular binding of TGFβ to its cell surface receptor. This is termed TGFβ activity. A reporter SMAD cell line (pGreenFire Lenti-SMAD Reporter, System Biosciences) was generated in Htert fibroblasts (htert-SMAD cells). The presence of active TGFβ induces SMAD binding to the reporter DNA and subsequent protein expression of GFP and luciferase reporter proteins.

A) htert-SMAD reporter cells were co-cultured with cells constitutively overexpressing USP10 (htert-USP10 cells) or control cells (htert-vector cells). Cell lysates were assayed for luciferase expression. htert-SMAD cells co-cultured with htert-USP10 cells showed 72%+/−27% higher luciferase activity *p<0.05, N=3.

B) Another cell line carrying the SMAD reporter was constructed, 293t-SMAD. These cells have high endogenous TGFβ activity thus allowing us to assess the affect of reducing USP10 gene expression with USP10 siRNA on TGFβ activity. 293t-SMAD cells were transiently transfected with USP10 and control siRNA. Cells treated with USP10 siRNA demonstrated a 35% decrease+/−9% compared to control siRNA *p<0.05. C) htert-SMAD reporter cells were co-cultured with cells constitutively overexpressing htert-USP10 cells in the presence of the integrin alpha v small molecule blocking agent (100 nM CWHM12) or control small molecule (100 nM CWHM96). Blocking αv integrins αvβ1, β3, β5 reduced USP10-mediated TGFβ activity by 63%+/−6% compared to control, *p<0.05 N=3.

FIG. 11 demonstrates that USP10 regulates the expression and organization of the key fibrotic markers, FN-EDA and α-SMA.

A) HCFs were transfected with USP10 or B) control cDNA. Cells were immunostained with antibody to FN-EDA. Images were captured on a Leica laser scanning confocal microscope. Bar=50 um.

C) Signal was quantified using MetaMorph Analysis software. USP10 overexpression induces an increase in FN-EDA (2.7 fold) compared to control. **p<0.01. These results were also demonstrated by Western blot.

D) HCFs were transfected with USP10 or control cDNA. Cell lysates were fractionated into DOC soluble and insoluble fractions and Western blotted for FN-EDA.

E) Gain and loss of USP10 affects α-SMA protein expression; increase 2.6-fold+/−0.4, decrease 3.5-fold+/−0.9, respectively.

F) USP10 overexpression increases the gene expression of αSMA and FN-EDA. qRT-PCR for USP10 (2.1+/−0.8), αSMA (1.4+/−0.1), and FN-EDA (4.2+/−1.1).

G) Htert-USP10 and htert-vector cells were immunostained for α-SMA. 50%+/−7% of USP10 over-expressing cells organize α-SMA containing stress fibers compared to none in control. Bar=50 um. N=3-5.

Figure 12:
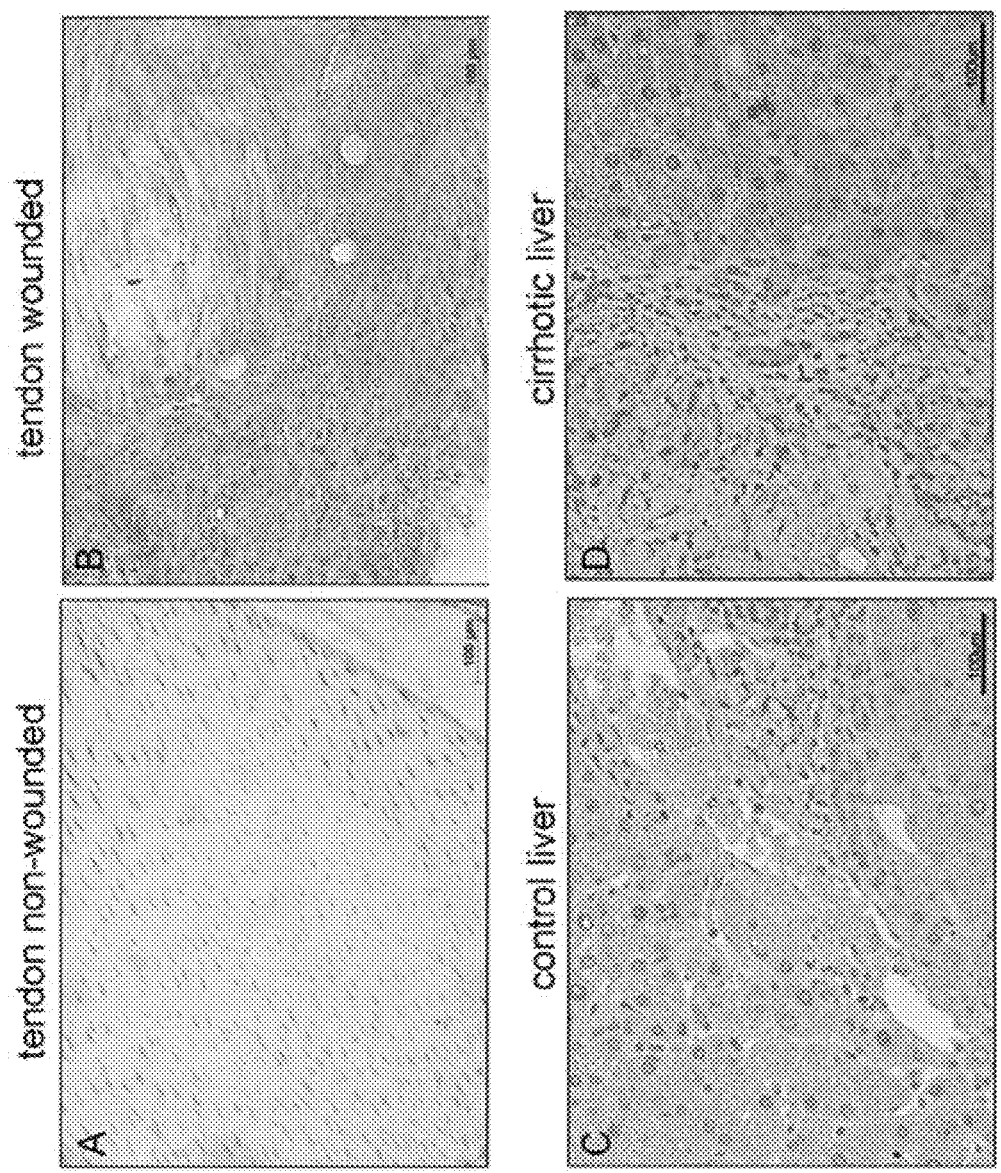

FIG. 12 demonstrates that USP10 is increased in vivo in non-ocular tissue after wounding and in diseased fibrotic tissue.

A, B) 13-week old male C57BL/6 mice remained uninjured (A) or underwent an excisional midsubstance defect (Beason et al., 2012) in the left patellar tendon using 0.75 mm biopsy punch (Shoney Scientific, Waukesha, Wis.) (B). Mice were sacrificed 1 week after injury, and their left patellar tendons were dissected, fixed in formalin, embedded in paraffin, and sectioned at 5 um in the coronal orientation. USP10 is increased 3.75-fold+/−1.26 *p<0.05. C,D) Deidentified cadaver non-fibrotic liver control (C) and cirrhotic liver (D) sections were obtained from the Biorepository and Pathology CORE at Mount Sinai. USP10 is increased 2.32+/−0.9. Bar=100 um. N=3.

DETAILED DESCRIPTION

The entire content of Provisional Application No. 62/092,552 filed on Dec. 16, 2014 and of Provisional Application No. 62/249,026 filed on Oct. 30, 2015 are incorporated by reference herein.

Ocular scarring leads to vision loss. For most fibrotic conditions in the eye, no therapies are currently available. We find that administration of an siRNA to USP10 not only prevents scarring but qualitatively promotes regenerative healing. Based on our substantial data on the role of the de-ubiquitinase (DUB) termed USP10 in the cornea, we demonstrate that reducing the protein expression of USP10 with an siRNA to USP10 will be an efficacious method to prevent the many manifestations of ocular scarring that are described in this application.

The broader term, RNA interference (RNAi) is a method for reducing the protein expression of a specific gene. A common type of RNAi is the use of doubled stranded siRNAs. These siRNA tools are 19 to 49 nucleotides in length and contain a "sense strand" and an "anti-sense" strand. Once inside the cell, the sense strand, which has the same nucleotide sequence as the "target" mRNA is removed. This leaves free, the anti-sense strand, which has a complimentary sequence to USP10 mRNA. The anti-sense siRNA binds to USP10 mRNA inducing a series of enzymatic reactions that prevents the translation of USP10 mRNA into USP10 protein, thereby "knocking down" USP10 protein expression. Most siRNAs have an efficiency of 50-90% and thus protein expression is usually reduced and not completely prevented.

Several methods are available to deliver siRNAs into cells. In cell culture (cells in a dish) siRNAs can be "transfected" (passed through the outer plasma membrane of a cell) by electroporation, a method in which the membrane is temporarily depolarized to allow the passage of nucleotides such as siRNAs. Lipid-mediated carriers can also be used to shuttle siRNAs through the plasma membrane or siRNAs can also be delivered to the inside of cells by self-delivery, a method in which a tag is engineered into the siRNA sequence that allows its passage through the plasma membrane. In organ culture (ex-vivo) and in vivo, lipid-mediated carriers, self-delivery siRNAs and also injection directly into the tissue site are methods that transport siRNAs inside the cells.

The molecular pathways and cell types that lead to scarring in all tissues are in part known. Scar tissue results from the persistence of myofibroblasts in a healing wound. Persistent myofibroblasts are overly adhesive cells that self-activate the fibrotic growth factor, TGFβ, leading to the overproduction of disorganized extracellular matrix, excessive contraction, and scarring. Global neutralization of TGFβ reduces myofibroblast differentiation but also prevents cell repopulation and wound closure, whereas a reduction in integrin-mediated local activation of TGFβ at the sight of injury will reduce the myofibroblast population and promote regenerative healing.

DUBs remove ubiquitin from substrate proteins. Thus increased DUB expression leads to reduced degradation and a resulting net increase in protein levels. Ubiquitination and de-ubiquitination control a vast array of cellular processes and thus inhibiting DUBs is considered as a desirable method to reduce aberrant disease-causing protein accumulation.

The cell-surface accumulation of integrins is a hallmark of myofibroblast development and scarring. Integrins are heterodimeric transmembrane proteins that bind to the extracellular matrix on the outside of the cell and to the cytoskeleton on the inside of the cell, thereby coordinating cell adhesion, cell tension, and cell migration.

The αv family of integrins: αv-β1, β3, β5, β6 play a significant role in causing fibrotic outcomes in all tissues. αv integrins drive myofibroblast persistence as they are heavily expressed on myofibroblasts and they self-activate TGFβ.

In the experimental work described herein, we show that USP10 controls the cell-surface protein levels of integrin αvβ5 and other αv-integrins specifically αvβ1 and αvβ3.

This effect of USP10 occurs in two pathways, one by increasing the quantity of myofibroblasts via preventing the degradation of integrin αvβ5 and in addition by causing enhancement of the presence of TGFβ.

In the eye as opposed to other tissues, scarring obstructs vision. Specifically, the cornea is the only transparent tissue in the body, making it an excellent model system to test for factors that induce scarring. Conditions that lead to scarring in the cornea are mechanical wounding, burns, viral and bacterial infections, and ulcers. Differentiation of cells (epthelial, stromal, and endothelial) into myofibroblasts during these healing events lead to scarring if the myofibroblasts do not apoptose (self-destruct) while healing. Here we demonstrate that reducing the gene expression of USP10 with siRNA to USP10 in the cornea prevents myofibroblast development and instead promotes regenerative healing.

Glaucoma is a disease where extracellular matrix accumulates in the trabecular meshwork, decreasing aqueous outflow and increasing pressure in the eye. Increased integrin-mediated cell adhesion of trabecular meshwork cells contributes to this transformation.

The surgery to relieve the pressure that is associated with Glaucoma is a trabeculectomy surgery. The "bleb" or flap that is made to relieve pressure often heals with a scar, reversing the benefit of the surgery. Currently mitomycin C treatment is used to halt all cell proliferation after surgery in an effort to stop this scarring outcome. This treatment is unpredictable and has safety concerns. The cells that proliferate and differentiation are called tenon fibroblasts. Reducing αv-integrins on tenon fibroblasts by decreasing USP10 gene expression with USP10 siRNA could promote regenerative healing after trabeculectomy surgery.

Another major point of fibrotic scarring in the eye is in the layer of epithelial cells called Retinal Pigmented Epithelial cells (RPE). The RPE layer of cells is adjacent to the retina. They are critical to vision and the correct functioning of the retina. The migration and proliferation of the RPE cells is called epithelial to mesenchymal transition (EMT), which leads to the development of fibrotic RPE myofibroblasts and a thick disorganized extracellular matrix covering the retina. Major diseases that either derive from or end with fibrotic outcomes in the RPE layer are age-related macular degeneration, diabetic retinopathy, and proliferative vitreoretinopathy.

Age-related macular degeneration (AMD) is the loss of photoreceptors in the central retina. Degeneration of the macula is associated with abnormal deposition of extracellular matrix called Drusen in the membrane between the RPE and the vascular choroid inducing a fibrovascular subretinal membrane leading to retinal scarring.

Proliferative Diabetic Retinopathy (PDR) is the more advanced stage of Diabetic Retinopathy, a disorder that develops in diabetic patients typically after a decade with the disease. An over accumulation of sugars damages the blood vessels in the retina. PDR is characterized by neovascularization into the retina. New aberrant blood vessels leak blood and growth factors that induce EMT ending in the development of fibrotic RPE myofibroblasts and a thick disorganized extracellular matrix covering the retina. This leads to retinal detachment.

Proliferative vitreoretinopathy (PVR) occurs after mechanical retinal detachment, fluid from the vitreous humor enters a retinal hole. During this process the RPE comes in contact with vitreous cytokines that induces EMT (fibrotic epithelial-derived myofibroblasts), which secrete disorganized extracellular matrix and fibrotic cytokines. This leads to scarring of the retina.

Based on our data in the cornea, a reduction in USP10 expression with USP10 siRNA is predicted to ameliorate all of these fibrotic conditions in the eye. Targeting the de-ubiquitinase (DUB), USP10 is a novel mechanism to promote regenerative wound healing.

To interrogate the role of USP10 in wound healing and fibrosis an ocular model system was used. The following listed materials and methods were used to create and to test the ocular model system and how it responds to the use of siRNA to USP10. The determinants of the subsequent results and how each was introduced into the experimental process are what are focused on in the listed materials and methods.

Materials and Methods

Cell Culture

Human cadaver corneas from unidentifiable diseased subjects were obtained from The National Disease Research Interchange (NDRI, Pittsburgh, Pa. Hence, the experiments performed in this report do not require their approval or waiver. Human primary corneal fibroblasts (HCFs) were derived from the stroma of human corneas obtained from NDRI. HCFs were isolated as described previously (Bernstein et al., 2007) and maintained in complete media (DMEM-F12 (Invitrogen) with 10% FBS (Atlanta Biologicals) with ABAM and Gentamicin (Invitrogen)). For experiments, except where noted, cells were plated on 10 ug/ml bovine collagen (Purcol, Advanced Biomatrix, Poway, Calif.) in supplemented serum-free media (SSFM): DMEM-F12 plus RPMI-1640 Vitamin Mix, ITS Liquid media supplement, 1 mg/ml glutathione (Sigma), 2 mM L-glutamine, 1 mM sodium pyruvate, 0.1 mM non-essential amino acids (Invitrogen) with ABAM and Gentamicin.

Organ Culture

Whole porcine eyes were obtained from Pel-freeze (Rogers, Ark.). Lids were removed from globe and eyes were submerged in 10% iodine and then rinsed thoroughly with PBS. A 6 mm trephine was used to wound the anterior cornea including the epithelium, basement membrane and anterior stroma and the excised tissue was removed with a surgical blade. Wounded and control (non-wounded) corneas were mounted on a mix of 1% agar, 1 mg/ml bovine collagen in DMEM-F12, and cultured for 2 weeks in SSFM plus 1 mM Vitamin C (2-0-aD Glucopyranosyl-Ascorbic Acid, Wako, Osaka, Japan). Gene knockdown was performed by treating cells with USP10 siRNA or siGLO siRNA with Lipofectamine 2000 (Invitrogen) by the standard protocol. After two-week incubation, during which the media was changed every 48 hours, tissue was fixed in 10% formalin and sections were generated at the Histology-Biorepository Shared Resource Facility at Icahn School of Medicine at Mount Sinai. 5 slices from each cornea in each experiment were analyzed. Using Image J, threshold pixel intensity was set for all images. The area greater than the threshold measurement in the corneal stroma was quantified for each image. All results are reported as ±SD. Statistical significance was assessed using a one-way ANOVA with Bonferroni's test.

Antibodies and Reagents

Integrin $\alpha v\beta 5$ antibody for immunocytochemistry (ICC), blocking, flow cytometry, and immunoprecipitation (IP) was from R & D Systems (MAB2528); integrin $\beta 5$ antibody for Western was from Abcam (ab15459). USP10 (Western) (8501), FLAG (2368), $\alpha v$ (4711), and GAPDH (2118) antibodies were from Cell Signaling. Fibronectin-EDA (ICC, histology) (F6140) and $\alpha$-Smooth Muscle Actin (ICC, histology) (C6198) were from Sigma. USP10 antibody for histology was from Bethyl Laboratories (A300-900A). Secondary Alexa-647 was from Molecular Probes, Eugene, Oreg. and all HRP-conjugated secondary antibodies were from Jackson Laboratories. Active recombinant USP10 protein was from Lifesensors. Magnetic HA-beads were from Pierce and Protein G Dynabeads were from Invitrogen. WT FLAG-ubiquitin lentiviral cDNA was a generous gift from Dr. Paul G. Galardy, Mayo Clinic, Rochester, Minn. Lentiviral cDNA USP10 (pLenti-GIII-CMV-hUSP10-Cterm-HA), and Vector (pLenti-III-Blank Control Vector) were from ABM Applied Biological Material. SMAD-luciferase/GFP reporter (pGFP-SMAD reporter cDNA; TR203PA-P) was from System Biosciences. The non-targeting fluorescent nucleotide control (siGLO) was from Dharmacon. USP10 siRNA was from Santa Cruz (sc-76811). USP10 cDNA (Flag-HA-USP10; 22543) for transient overexpression was from Addgene.

Transient Transfections and Cell Lines

Transient transfection was performed using the Amaxa Nucleofection system (Gaithersburg, Md.) and Lonza P3 reagent. HCFs were transfected using 10 mM USP10 siRNA or control siRNA (siGLO), or 1.5 ng USP10 cDNA or control cDNA, and seeded on collagen in SSFM without antibiotics. Cells were analyzed after 24-48 hours. Knockdown/overexpression was confirmed by Western blot and RT-PCR.

For sustained vector expression, cell lines were created using standard lentiviral infection technique: SMAD-luciferase/GFP reporter (pGreenFire Lenti-Reporter, System Biosciences) with immortalized htert HCFs (htert-SMAD); SMAD-luciferase/GFP reporter (pGreenFire Lenti-Reporter, System Biosciences) with 293t (293t-SMAD); USP10 overexpressing immortalized htert HCFs (htert-USP10); Empty vector overexpressing immortalized htert HCFs (htert-vector); Ubiquitin-FLAG vector overexpressing immortalized htert HCFs (htert-ubiquitin). Selection was by puromycin (htert-SMAD, htert-USP10, 293t-SMAD) or hygromycin (htert-ubiquitin).

Immunocytochemistry (ICC) and Blocking $\alpha v\beta 5$ with Antibody

Cells were fixed with 3% paraformaldehyde (Fisher Scientific, Fair Lawn, N.J.), permeabilized with 0.1% Triton X-100 (Sigma), and blocked with 3% normal mouse serum (Jackson Immuno Research). Cells were incubated in primary antibody to SMA-cy3 or Fibronectin-EDA. Cy5 conjugated goat-anti-mouse IgM was used as a secondary to Fibronectin-EDA. SMA-cy5 stained coverslips were viewed with a Zeiss Axioskop microscope and images were captured using a Zeiss Axioplan2 microscope with a SPOT-2 CCD camera (Diagnostic Instruments, Sterling Heights, Mich.). Fibronectin-EDA stained coverslips were imaged using Leica SP5 confocal microscope, and signal was quantified by Metamorph software. To block integrin $\alpha v\beta 5$, 2.5 ug/ml $\alpha v\beta 5$ blocking antibody or IgG control was added to coverslips after cells attached (2 hours). Immunostaining for FN-EDA was performed 48 hours after cell seeding. Imaging was performed at the Microscopy Shared Resource Facility at Icahn School of Medicine at Mount Sinai.

Flow Cytometry 2.5 ug/mL antibody was added to cell plates for 1 hour at 4° C. with rocking. Cells were detached with Cell-Dissociation Solution, non-enzymatic (Sigma) with 0.05% sodium azide at 37° C. and centrifuged. Cells were re-suspended at $1\times 10^6$ cells/ml in PBS supplemented with 3% BSA. 400,000 cells were centrifuged and re-suspended in Alexa 488 secondary antibody diluted in PBS with 3% BSA and incubated for 30 minutes. After washing, cells were stained with PI$\alpha$ and analyzed in a flow cytometer (Accuri c6).

Western Blots

Cells were lysed in RIPA buffer (0.1% SDS, 0.05M Tris, 0.15M NaCl, 0.5% Na Deoxycholate, 1% Triton) plus complete protease inhibitor tablet (Roche) and PMSF (Fisher Scientific). 15 mg protein was separated on 10% NuPAGE gels under reducing conditions (except for integrin $\beta 3$, which is run under non-reducing conditions) and transferred to PVDF membranes. Primary antibody was added to 5% BSA in TBST and secondary antibody was added to 1% milk in TBST. Bands were visualized using CL-XPosure Film (Thermo Scientific). Fibronectin DOC soluble and insoluble western blots were performed using protocol previously described by (Sechler et al., 1996).

Immunohistochemistry

Porcine Cornea IHC: Slides were deparaffinized using SafeClear (Protocol, Fisher Healthcare, Philadelphia, Pa.) for 2 times 10 minutes, then transferred into 100% EtOH, 70% EtOH, 50% EtOH, ddH20 for 5 minutes each. Slides were then microwaved at 50% power for 2 times 5 minutes in citrate buffer for antigen retrieval. After cooling, slides were washed in PBS and placed in 1° A Triton in PBS for cleaning. Tissue was then blocked with 3% normal goat serum in PBS for 1 hour, and then treated with primary antibody overnight. After washing in 0.1% Tween PBS, slides were placed in 3% $H_2O_2$ for 10 minutes to block endogenous peroxidase. Tissue was then incubated with HRP secondary antibody (1:200) for 1 hour. After washing in 0.1° A Tween PBS, tissue was treated with DAB kit (Vector Laboratories, Burlingame, Calif.). Tissue was counterstained in Harris Modified Hematoxylin (Fisher Chemical, Philadelphia, Pa.) and stained with Scott's Bluing Reagent (Ricca Chemical Company, Pokomoke City, Md.), before dipping in ddH20, 50% EtOH, 70% EtOH, 100% EtOH, and SafeClear. After drying, slides were mounted with mounting medium (Trevigen, Gaithersburg, Md.). Imaging was performed using the Axioplan 2 microscope in the Icahn School of Medicine Microscopy Shared Resource Facility.

RNA Extraction and Real-Time PCR

TRI Reagent RT kit (MRC, Cincinnati, Ohio) was used to extract total RNA from cell lysates. RNA was cleaned with RNeasy Mini Elute Cleanup Kit (Qiagen, Valencia, Calif.). cDNA was generated from 1 mg of total RNA using the Superscript First Strand and oligo dT (Invitrogen). Absolute Blue qPCR master mix (Fisher) was used to generate PCR product. Triplicate determinations were analyzed using the ABI 7900 sequence detection system. Annealing temperature was 55° C. for all reactions. Primers used:
$\beta 5$ (IDT): CTGTCCATGAAGGATGACTT, TGTCCACTCTGTCTGTGAGA;
$\alpha v$ (IDT): GTGGACAGTCCTGCCGAGTAC, GAGCTCCCACGAGAAGAAACA;
GAPDH (Invitrogen): TTGATTTTGGAGGGATCTCG, GAGTCAACGGATTTGGTCGT;
Fibronectin-EDA (IDT); TCCAAGCGGAGAGAG, GTGGGTGTGACCTGA;
SMA (IDT): CATCTCGTTTTCAAAGTCCAGAGC, TGAGCGTGGCTATTCCTTCGT
USP10 (IDT): GATCCTCTGAAACCGGAACA, AGAGTGCATCACCTCCTGCT.

Recycling Assay

HCFs transfected with USP10 or control cDNA were seeded on collagen-coated coverslips in SSFM. After 24 hrs, 2.5 ug/ml anti-$\alpha v \beta 5$ mouse antibody was added to each well and the cells were incubated at 37° C. for 30 minutes to allow for antibody-integrin internalization. Antibody remaining on the cell surface was blocked with goat antimouse antibody for 30 minutes at RT. Cells were incubated for 90 min at 37° C. to allow for integrin $\alpha v \beta 5$-recycling to the cell surface prior to fixation with 2% PFA with 30% sucrose (30% sucrose reduces PFA-induced membrane permeabilization) (Strachan and Condic, 2004). Stained cells were imaged with identical exposure times by wide field microscopy. $\alpha v \beta 5$ signal per cell was quantified by MetaMorph Image Analysis software.

TGF$\beta$ Activity Assays

TGF$\beta$ activity was measured using cell lines constitutively expressing pGreenFire Lenti-Reporter (System Biosciences) a reporter for SMAD activation. This reporter was used to generate TGF$\beta$ reporter cell lines with htert fibroblasts (htert-SMAD) and 293t cells (293t-SMAD). To assess TGF$\beta$ activity with USP10 overexpression, 50K Htert-SMAD cells were co-cultured with 50K cells constitutively overexpressing USP10 (htert-USP10) or control cells (htert cells expressing empty vector, htert-vector cells). After 24 hours, cells were removed with trypsin, pelleted, re-suspended in luciferase reagent, placed in wells in triplicate, and assayed for luciferase expression. To assess TGF$\beta$ activity when USP10 was silenced, USP10 and control siRNA were transiently transfected in 293t-SMAD cells and assayed as above. To assess TGF$\beta$ activity when av integrins were blocked, USP10 cells were treated with intergrin $\alpha v$ blocking small molecule or matched control small molecule and assayed as above.

USP10 DUB Assays

Ubiquitin Immunoprecipitation: HCFs were transfected with USP10 siRNA or siGLO and seeded in SSFM. After 24 hours, chloroquine (Enzo Life Sciences) was added to a final concentration of 10 uM to inhibit lysosomal degradation. After 24 hours in chloroquin, cells were lysed in RIPA with protease inhibitors, phosphatase inhibitor (HALT), and DUB inhibitors (NEM and PR619). Lysate was incubated overnight with anti-FLAG beads (Clonetech). The beads were washed and incubated for 5 minutes at 100° C. Eluted proteins were separated on 4-12% NuPAGE gels, transferred to PVDF membrane, and Western blotted for $\beta 5$.

Integrin $\alpha v \beta 5$ Immunoprecipitation

Dynabeads Protein G magnetic beads (Invitrogen) were incubated with $\alpha v \beta 5$ antibody 1 hr at 4° C. Htert-ubiquitin cells were lysed with 1% Triton buffer (1% Triton, 150 mM NaCl, 20 mM Tris, pH 7.5) with protease inhibitors, phosphatase inhibitor (HALT), and DUB inhibitors (NEM and PR619). Lysate was added to the antibody pre-bound beads and incubated overnight. 20 nM active recombinant USP10 protein was added to assay buffer (Tris-buffered saline, pH 7.5, with 2 mM $\beta$-Mercaptoethanol and 0.02% Tween20). USP10 was inactivated by incubating with 10 mM PR618 and 10 mM NEM for 30 minutes at 30° C. Beads were isolated with a magnet, washed, and suspended in assay buffer with active or inactive USP10 for 30 minutes at 30° C. Beads were pulled out with a magnet, washed, and suspended in reducing sample buffer. After 5 minute incubation at 100° C., samples were separated on 4-12% NuPAGE gels, transferred to PVDF membrane, and Western blotted for FLAG.

Statistical Analysis

Numerical data are expressed as the mean+/−SD of 3-5 independent experiments. Statistical significance for histological analysis of three groups (non-wounded, wounded plus control siRNA, and wounded plus USP10 siRNA) was calculated by one-way ANOVA with Bonferroni's test. Statistical significance of all other numerical data was calculated with the Student's t-test. *p value<0.05, p value<0.01, *p value<0.001.

Upon completion of the above methods, USP10 was shown to inhibit the degradation of the specific integrin $\alpha v \beta 5$ protein that promotes the persistence of myofibroblasts. The following listed results illustrate how the agent siRNA is used in the ocular model system to promote regenerative healing after wounding. Although the experimental work was done on the cornea, it is considered that the results are equally applicable to the entire ocular system and in fact can be considered more general as well because the particular findings are not dependant on the tissue model but rather on the operative factors (molecular mechanisms of the USP10 pathway) as seen in the experiments and results.

Results

We have used a corneal tissue model system to interrogate the role of USP10 in wound healing and fibrosis. After stromal wounding or corneal infection the presence of myofibroblasts and the disorganized newly deposited fibrotic matrix prevents the transmission of light through the cornea. Preventing scarring in the eye is uniquely important since ocular scarring leads to vision loss.

Corneal Physiology

Figure 1:
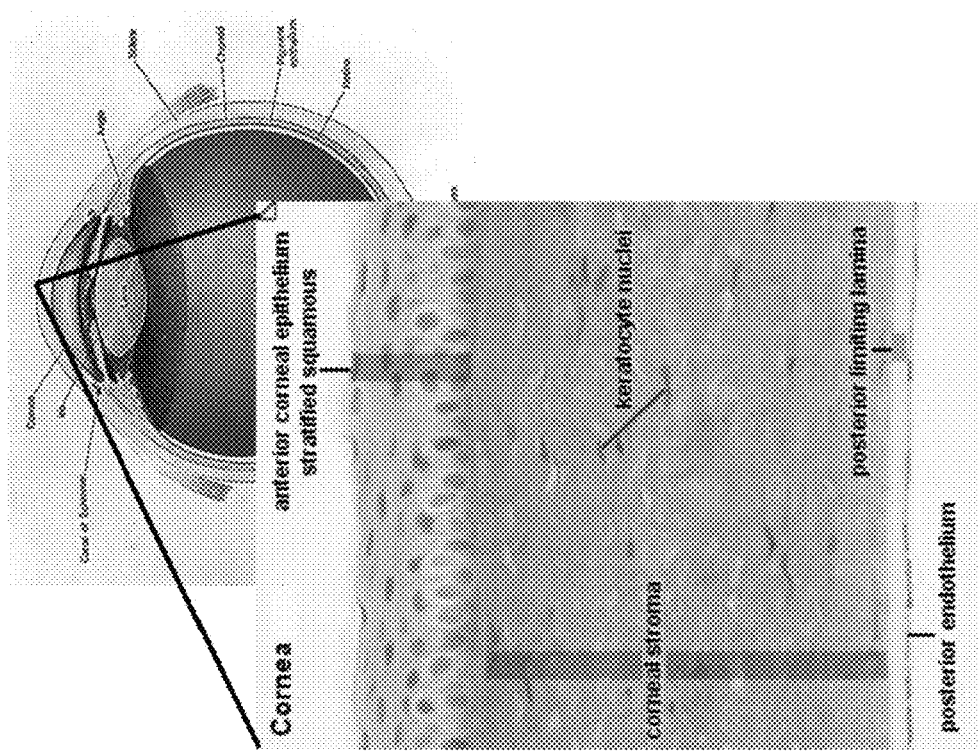
FIG. 1 is a picture of an eye and an explanation of corneal physiology.

FIG. 1 is a picture of an eye and an explanation of corneal physiology. The cornea has a stratified epithelium with an underlying basement membrane. 90% the depth of the cornea is the corneal stroma containing quiescent keratocytes embedded in a perfectly organized transparent lattice of collagen and proteoglycans. The corneal endothelium is a monolayer of cells that controls the flow of solutes into and of the cornea. The function of the cornea in the eye is to focus incoming light onto the lens and the retina and for the protection of the eye.

Wound Healing in the Corneal Stroma

Wounding through the epithelium and underlying basement membrane induces fibrotic scarring in the anterior stroma. The normally quiescent keratocytes differentiate into fibroblasts that migrate into the wound site. Fibroblasts differentiate into myofibroblasts that function to close the wound, however, the persistence of myofibroblasts in a wound results in scarring in the cornea and in all tissues in the body. We demonstrate in this proposal that reducing the number of myofibroblasts after wounding not only prevents fibrotic scarring but also induces a regenerative healing program. The cornea is an excellent model system to study agents that promote regenerative healing because of the accessibility of human tissue and the ability to perform organ culture studies. This is sequence of events is depicted in FIG. 2.

Overview

In FIG. 3 is a schematic diagram depicting the induction of USP10 protein expression after wounding generates persistent myofibroblasts leading to fibrotic scarring. These data were generated in human corneal stromal fibroblast cell culture and in porcine corneal organ culture. We demonstrate that:

a) after wounding, TGFβ that is secreted from local sources (in the cornea, the epithelium) induces the protein expression of the de-ubiquitinase (DUB), USP10 (FIG. 4). Whereas, the reduction of USP10 gene expression with siRNA to USP10 after corneal wounding prevents the expression of fibrotic markers and promotes regenerative healing (FIG. 5).

b) USP10 post-translationally regulates integrin αvβ5 by removing ubiquitin. This action promotes the recycling of integrin αvβ5 back to the cell surface where it accumulates instead of being degraded inside the cell (FIGS. 7 and 8). USP10 also promotes the accumulation of the other alpha v integrins, αvβ3 an αvβ1 (FIG. 9).

c) USP10 over-expression induces TGFβ activity (because the accumulation of integrin αv protein on the cells surface, FIG. 10).

d) Increased cell-surface integrin-mediated adhesion and TGFβ activity induces the expression and organization of FN-EDA and α-SMA containing stress fibers, key fibrotic markers (FIG. 11).

e) Description of the siRNAs used to prevent ocular scarring (FIG. 13).

USP10, Integrin αvβ5 and α-SMA Expression are Increased after Wounding

All experiments were repeated 3-6 times.

A sharp-edged cylinder (trephine) is used to create a wound through the epithelium, basement membrane and the anterior stroma with subsequent removal of the incised tissue. The corneas are then mounted on an agar base and cultured for up to 1 month[4]. The limbal conjunctiva was covered with supplemented serum-free medium (SSFM) with 1 mM Vitamin C, and the exposed epithelium was moistened daily for 2 weeks.

In this type of wound, stromal myofibroblasts are induced in response to factors secreted by the wounded epithelium such as IL-1, TGFβ and PDGF without exogenous growth factors. IL-1 induces apoptosis of the quiescent stromal cells termed keratocytes in the wound margin. TGFβ plays key roles in activating peripheral keratocytes into motile fibroblasts that repopulate the wound margin and then terminally differentiate into wound contracting myofibroblasts. In this type of wound myofibroblasts persist, leading to opacity and scarring.

In this ex-vivo model, just 1 week after wounding, myofibroblasts (α-SMA detection) were reproducibly generated in the wounded anterior stroma without TGFβ addition (data not shown). Their number increased at 2 weeks and this time point was used in our studies to collect histological data. In FIG. 4 we demonstrate that compared to control fibrotic markers increased in the anterior stroma after wounding: (A, B) α-SMA 2.9-fold+/−0.8 *p<0.005, (C) No primary antibody control, (D, E) USP10 2.5-fold+/−0.8 p<0.01, and F) Pre-incubation with a USP10 blocking peptide reduced immunostaining. Bar=50 um.

Culturing cells in serum induces a wounding phenotype. To confirm the organ culture results in cell culture, we tested if culturing human and pig primary corneal epithelial cells and corneal stromal fibroblasts (cultured, C) compared to cells lysed directly after isolation from the tissue (non cultured, NC), would induce an increase in the expression of USP10. The data in FIG. 4G demonstrate that in both human and porcine epithelial cell and stromal fibroblasts, USP10 expression is induced in culture cells compared to freshly isolated cells, supporting our model that USP10 is induced upon wounding.

TGFβ Induces USP10 Protein Expression.

Since TGFβ plays an important role in all wounding and fibrotic disease, we tested if TGFβ induced the expression of USP10. In the remaining cell culture studies unless otherwise noted, fibroblasts that have been passaged in serum-containing media are detached and plated on type I collagen in supplemented-serum free media (SSFM). In FIG. 4H, primary human corneal fibroblasts (HCFs) were treated with 1 ng/ml TGFβ for 2 days. TGFβ increased USP10 expression by 57% as compared to no treatment. Blocking TGFβ-induced SMAD2/3 signaling with the TGFβRI/II-SMAD2/3 inhibitor (SB431542) decreased USP10 expression by 44%, demonstrating that USP10 expression is induced at least in part through TGFβ-SMAD 2/3 signaling. Together these data suggest that wounding and the TGFβ pathway play a role in inducing USP10 expression.

USP10 Silencing with USP10 siRNA Prevents Fibrotic Healing

To test if USP10 silencing would decrease fibrosis and improve healing, we targeted USP10 with siRNA after wounding in our ex-vivo organ culture model (FIG. 5). Because USP10 is a well-conserved gene, we tested and confirmed that siRNA made to human USP10 targets the porcine USP10 homolog. (FIG. 5A). Next, directly after wounding, the wounded area was treated with USP10 or control siRNA complex with Lipofectamine2000 (Invitrogen). After 3 hours the siRNA was diluted with culture media. After 2 weeks, corneas were fixed and analyzed by immunohistochemistry. We hypothesized that an initial reduction of USP10 gene expression would redirect signaling from a fibrogenic program into a regenerative healing program. In FIG. 5B-M, we demonstrate that USP10 siRNA decreased USP10, integrin αvβ5, α-SMA, and FN-EDA. After addition of USP10 siRNA, USP10 is reduced 2-fold+/−0.6 p<0.01; integrin αvβ5 3.7-fold+/−1.2 p<0.01; α-SMA 2.2-fold+/−0.6 *p<0.005; and FN-EDA 3.3-fold+/−1.2 p<0.01. Immunostaining of wounded corneas treated with USP10 siRNA were equal to non-wounded controls in all experiments; comparisons of means between control and USP10 knockdown were non-significant. Bar=50 uM. N=3-5. 5 slices from each cornea in each experiment were analyzed. A threshold pixel intensity was set for all images. Area greater than the threshold measurement was quantified for each image. Statistical significance calculated by one-way ANOVA with Bonferroni's test. Here we conclude that when compared to the control siRNA and USP10 silencing prevents the effects of the endogenous TGFβ that is secreted into the stroma after wounding. Importantly, the epithelium re-grew and stratified. Qualitatively, we also noticed that USP10 knockdown improves cell and matrix alignment in the stroma, which is a critical component of regenerative healing in the cornea.

SLUG is Expressed in the Corneal Epithelium after Wounding.

SLUG is a marker for what is termed EMT, the transition of epithelial cells to fibroblast-like cells. Since we observed staining in the epithelium for αvβ5 and other fibrotic markers, we hypothesized that the epithelium after wounding was going through a transition to a fibroblast/myofibroblast phenotype. In this experiment (FIG. 6), porcine corneas were cultured as in FIG. 4 and were either A) unwounded (control) or B) wounded and treated with control siRNA or C) wounded and treated with USP10 siRNA. Sections were immunostained with anti-SLUG antibody. After treatment of the wounded cornea with USP10 siRNA, SLUG staining decreased 4.4-fold+/−1.3 *p<0.05 compared to control siRNA. These data demonstrate that corneal wounding induces EMT (differentiation of epithelial cells into myofibroblasts in the regrown epithelium) and that siRNA to USP10 significantly reduces this transition in this cell layer.

USP10 Post-Translationally Regulates Integrin αvβ5

Pathological myofibroblasts have elevated cell-surface expression of integrin αvβ5. We found that that USP10 affects the protein expression of integrin αvβ5. HCFs were transfected with USP10-cDNA or control vector; USP10 siRNA or control siRNA (FIG. 7A). Cell lysates were Western blotted for USP10, integrin β5, αv, and GAPDH. USP10 overexpression increases β5, (3.3 fold+/−0.4) and αv (3.3+/−1.0). USP10 silencing decreases β5 (90%+/−5%) and αv (88%+/−28%) (Exposure times vary between cDNA and siRNA experiments and thus band densities between the two cannot be compared). Moreover, over-expression of USP10 increased cell surface levels of integrin αvβ5 (2-fold+/−0.5, *=p<0.05 as quantified by flow cytometry (FIG. 7B). Next we tested if the increase in cell surface integrin αvβ5 was because non-degraded integrin was returning (recycled) to the cell surface. In this experiment HCFs were transfected with either USP10 or control cDNA. After 48 hours, cells were treated with antibody to integrin αvβ5 for 30 minutes at 37° C. to allow for antibody internalization. The cell surface was then blocked with unlabeled secondary antibody prior to incubation again at 37° C. for 90 minutes. Primary antibody that was recycled to the cell surface was detected with fluorescently labeled secondary antibody after cell fixation. Cells were imaged with identical exposure times. The αvβ5 signal is quantified by MetaMorph software. 70 cells/condition/experiment. (75% increase+/−9%, **=p<0.01 (FIG. 7C). Finally to test if the impact of USP10 gene expression on integrin αvβ5 gene expression, using RT-qPCR we found that integrin αv or β5 RNA expression was not significantly altered by USP10 over-expression (FIG. 7D). Together, these data demonstrate that USP10 acts post-translationally to affect β5 protein levels.

USP10 is a DUB for Integrin αvβ5

Although we have demonstrated that USP10 post-translationally regulates protein levels of integrin αvβ5, it was still unknown if this was a direct affect of USP10 acting on integrin αvβ5 or through intermediates. Thus we tested if USP10 removes ubiquitin from integrin β5. For this experiment, a cell line that over-expresses ubiquitin linked to a FLAG tag was created in htert immortalized fibroblasts (htert-ubiquitin cells). In FIG. 8A htert ubiquitin-FLAG cells were transfected with USP10 siRNA or control siRNA in the presence of 10 uM chloroquin. Lysates were immunoprecipitated with anti-FLAG beads. Eluted proteins were Western blotted for integrin β5, USP10 and GAPDH. Ubiquitinated β5 is increased 1.9-fold+/−0.5 after treatment with USP10 siRNA compared to control siRNA. In FIG. 8B, htert-ubiquitin-FLAG cell lysates were immunoprecipitated with antibody to integrin αvβ5. The IP was either not treated or treated with 20 nM active or inactivated recombinant USP10 protein the presence of the DUB inhibitors, N-ethylmalimide and PR-619. Eluted proteins were Western blotted for FLAG. After addition of recombinant USP10, β5 ubiquitination is decreased by 2.6-fold+/−0.9. N=3. These experiments demonstrate that USP10 is a DUB for integrin β5.

USP10 Regulates Other Alpha v Integrins.

Work in other fibrotic systems demonstrates that all of the alpha v integrins are involved in inducing fibrosis. Therefore we tested if USP10 affects other alpha v integrins that are expressed in the corneal myofibroblasts (FIG. 9). HCFs were transfected with USP10-cDNA or control vector. Cell lysates were Western blotted for USP10, integrin β3, β1, and GAPDH. USP10 overexpression increases Integrin β1 (3.9+/−1.1) and Integrin β3 (2.0+/−0.1). These data in conjunction with our other Western blots (FIG. 4) show that αvβ3 and αvβ1 are also affected by USP10 protein expression.

USP10 Induces TGFβ Activity

It was previously reported that integrin αvβ5 directly activates TGFβ in myofibroblasts. Our working model is that wounding-induced USP10 will generate an autocrine loop of TGFβ activity by upregulating αvβ5 (and other αv integrins). Thus, we hypothesized that since USP10 over-expression increased cell surface αvβ5 that in turn, TGFβ activity should increase. To test this, we created an htert-HCF cell line with a SMAD reporter that contains SMAD-DNA binding elements. In this system, TGFβ signaling induces SMAD-reporter binding and subsequent induction of both GFP and luciferase. First we confirmed that the htert-HCF line had low (undetectable) endogenous TGFβ activity so that the induction of TGFβ activity by USP10 could be quantified (data not shown). Next we co-cultured htert-HCF USP10 cells or htert-HCF control vector cells each with htert-HCF SMAD for 24 hours in SSFM. The next day, cells were lysed and luciferase substrate (Brightglo) was added prior to quantification of luciferase activity in each sample. In FIG. 10A we demonstrate that USP10 cells induce a 73%+/−22% increase in TGFβ activity (p<0.01). Then, to demonstrate that in general, αv integrins activate TGFβ, htert-HCF USP10 cells were treated with a small molecule proven to block αv integrin activity (CWHM12) or its control small molecule (CWHM96). Blocking αv integrins on these cells (αvβ1, β3, β5) reduced USP10-mediated TGFβ activity by 63%+/−6% compared to control, *p<0.05 N=3.

To test if silencing USP10 gene expression would decrease TGFβ activity we created a SMAD reporter cell line in 293t cells that have high endogenous TGFβ activity (data not shown). Unlike the co-culture experiment above, USP10 gene expression was silenced with USP10 siRNA in these SMAD reporter cells compared to control siRNA. After 24 hours cells were counted. Equal numbers of cells were lysed with luciferase substrate. In FIG. 10B we report a consistent 33%+/−5% (p<0.01) decrease in TGFβ activity when USP10 is silenced.

USP10 Over-Expression Induces FN-EDA and α-SMA Expression and Myofibroblast Differentiation Since USP10 overexpression increased TGFβ activity, we next tested if USP10 induced other fibrotic markers. The expression of the EDA splice variant of Fibronectin (FN-EDA) is a key marker for fibrotic disease. Thus we tested if USP10 would increase FN-EDA expression in HCFs. To test this, HCFs were transfected with USP10 or control vector cDNA. After 48 hours, cells were immunostained for FN-EDA and imaged by confocal microscopy. In FIG. 11A,B, we demonstrate that USP10 overexpression induces a dramatic increase in FN-EDA (2.7 fold). FN-EDA expression was quantified using MetaMorph Analysis software and represented in FIG. 11C. Images were captured on a Leica laser scanning confocal microscope. Bar=50 um. 10 images from 5 experiments per condition were quantified. Student t-test shows significance between USP10 cDNA and each condition, p<0.01. These results were also demonstrated by Western blot D) HCFs were transfected with USP10 or control cDNA. Cell lysates were fractionated into DOC soluble and insoluble fractions and Western blotted for FN-EDA (FIG. 11D).

α-SMA expression and organization is a central characteristic of the myofibroblast phenotype. We found that USP10 gain and loss of gene expression affected α-SMA protein expression. In FIG. 11E we demonstrate that HCFs transfected with USP10 cDNA compared to control vector cDNA increased protein expression, where as USP10 siRNA compared to control siRNA reduced α-SMA protein expression. Increase, 2.6-fold+/−0.4, decrease 3.5-fold+/−0.9, respectively. USP10 also increased α-SMA and FN-EDA gene expression by demonstrated by RT-PCR (FIG. 11F). USP10 (2.1+/−0.8), αSMA (1.4+/−0.1), and FN-EDA (4.2+/−1.1).

In addition to α-SMA expression, the organization of α-SMA containing stress fibers is a fundamental part of myofibroblast biology and cell contraction. The importance of integrin αvβ5 to the development of myofibroblasts has been previously demonstrated. The appearance of α-SMA stress fibers is mediated by an increase in integrin-ECM binding. In FIG. 11G we demonstrate that 50%+/−7% of USP10 over-expressing cells organize α-SMA containing stress fibers compared to none in control. Bar=50 um. N=3-5. Both α-SMA protein expression and increased adhesion are required for the organization of α-SMA containing stress fibers, the key component marker of myofibroblast differentiation. Thus, here we have demonstrated that an increase in USP10 protein expression induces myofibroblast differentiation.

USP10 is Increased In Vivo in Other Scarred and Fibrotic Tissues.

To demonstrate that an increase in USP10 after wounding is not specific to the cornea, we immunostained wounded (scarred) mice tendons (non-wounded, FIG. 12A, wounded FIG. 12B), USP10 is increased 3.75-fold+/−1.26 *p<0.05 in wounded tendons. Deidentified cadaver non-fibrotic liver control FIG. 12C and cirrhotic (fibrotic) liver FIG. 12D sections were obtained from the Biorepository and Pathology CORE at Mount Sinai. USP10 is increased 2.32+/−0.9. Bar=100 um. N=3.

siRNAs Used to Prevent Ocular Scarring

The present invention relates to the use of interfering RNA for inhibition of expression of USP10 in ocular disorders. Here we show the human DNA sequence for USP10 and the 3 siRNAs from Santa Cruz Biotechnology and having a 3'TT overhang (SEQ ID NO 2-7, FIG. 13), which we used to demonstrate that USP10 siRNA prevents fibrotic healing. SEQ ID NO:1 corresponds to the mRNA for human USP10. The mRNA is identical to the DNA sequence with the "T" residues replaced with "U" residues. Thus it is the anti-sense strand of the double stranded USP10 siRNA that is complementary to and binds to the USP10 mRNA inside the cell. Binding of USP10 siRNA to USP10 mRNA causes the destruction of USP10 mRNA. Since mRNA is translated into protein, the destruction of USP10 mRNA prevents or in most cases, reduces, the protein expression of USP10. The percent of knock-down is usually measured by determining the mRNA levels by qRT-PCR, by Western blot or by ELISA. We have found that reducing the protein expression of USP10 promotes regenerative ocular wound healing.

Although we have used 3 specific USP10 siRNAs to knock down USP10 protein expression, the invention allows for any USP10 siRNA that is used to target human USP10 mRNA. In general, 100% sequence complementarity between the antisense strand of siRNA and the target mRNA is typical for siRNA design but it is not required under the present invention. siRNA sequences that are based on the target sequence but with insertions, deletions, or point mutations are effective for inhibition. The target sequence of SEQ ID NO:1 may be in either the 5' or 3' untranslated regions of the mRNA or in the mRNA coding region. The double-stranded siRNA may have a 3' overhang of from 1 to 6 nucleotides on either one or both of the strands. Interfering RNA may be as single stranded or double stranded siRNAs, or interfering RNA may be expressed from a plasmid using a constitutive or inducible promoter, or from a viral vector.

Together our data demonstrate the novel discovery that USP10 expression is a critical modulator of scarring in the eye and that attenuating its protein expression or activity with siRNA to USP10 prevents scarring outcomes.

Mode of administration: Interfering RNA may be delivered directly to the eye by ocular tissue injection; by direct application to the eye, by topical ocular drops or ointments; or by a slow release device.

Subject: This invention will be applied to a subject for the treatment for an ocular disorder or someone who may develop an ocular disorder. This may include, corneal wound healing or disease, glaucoma, wound healing after trabeculectomy surgery that is associated with glaucoma, age-related macular degeneration, diabetic retinopathy, and proliferative vitreoretinopathy.

Acceptable carriers. An acceptable carrier for ophthalmology is one that causes little to no irritation in the eye, provides suitable preservation when needed with one or more USP10 siRNAs. USP10 siRNA may be combined with preservatives, solvents, surfactants, enhancers of viscosity or penetration, buffers, salts, or water to yield a sterile suspension or solution for ocular treatment.

SEQUENCE LISTING: The sequence of the human USP10 gene from the GenBank database of the National Center for Biotechnology Information at ncbi.nlm.nih.gov.

SEQ ID NO: 1. NCBI Reference Sequence: NM_001272075.1

| | | | | | | |
|---|---|---|---|---|---|---|
| 1 | | | | | | |
| cuccccgcgc | cccgcggcgc | gcggccagug | cgcaggcgcg | gcggccgaug | cgagugugua | 60 |
| ugugcgggcg | agaagauggc | ggcggcgggg | gaagcagcgu | gagcagccgg | aggaucgcgg | 120 |
| agucccaaug | aaacgggcag | ccauggcccu | ccacagcccg | cagcuccugg | gccaugaucc | 180 |
| cauuuucauc | agaugacuug | agaacccaga | agcucuacca | gcacugccau | ucugucccgu | 240 |
| cuugaaacau | caugcccugg | uugcccucuc | cuggaauagg | gcaguauauu | uuggagauu | 300 |
| uuagcccuga | ugaauucaau | caauucuuug | ugacuccucg | aucuucaguu | gagcuuccuc | 360 |
| cauacagugg | aacaguucug | uguggcacac | aggcugugga | uaaacuaccu | gauggacaag | 420 |
| aauaucagag | aauugaguuu | gguguucgaug | aagucauuga | acccagugac | acuuugccga | 480 |
| gaaccccccag | cuacaguauu | ucaagcacac | ugaaccccuca | ggccccugaa | uuuauucucg | 540 |
| guuguacagc | uuccaaaaua | accccugaug | guaucacuaa | agaagcaagc | uauggcucca | 600 |
| ucgacugcca | guaccccaggc | ucugcccucg | cuuuggaugu | aaguucuaau | guggaggcgu | 660 |
| aaguuuugga | aaaugauggu | gucucaggug | gucuuggaca | aggggagcgu | aaaaagaaga | 720 |
| aaaagcggcc | accuggauau | uacagcuauu | ugaaagaugg | uggcgaugau | aguaucucca | 780 |
| cagaagcccu | ggucaauggc | caugccaauu | cagcagucccc | gaacagugucc | agucagagg | 840 |
| augcagaauu | uaugggugac | augccccccgu | caguuacgcc | caggacugu | aacagccccc | 900 |
| agaacuccac | agacucuguc | agugacauug | ugccugacag | uccuuucccc | ggagcacucg | 960 |
| gcagugacac | caggacugca | gggcagccag | aggggggccc | cgggggcugau | uuuggucagu | 1020 |
| ccugcuuccc | ugcagaggcu | ggcagagaca | cccugucaag | gacagcuggg | gcucagcccu | 1080 |
| gcguuggguac | cgauacuacu | gaaaaccuug | gaguugcuaa | uggacaaaua | cuugaauccu | 1140 |
| cgggugaggg | cacagcuacc | aacggggugg | aguugcacac | cacggaaagc | auagacuugg | 1200 |
| acccaaccaa | acccgagagu | gcaucaccuc | cugcugacgg | cacgggcucu | gcaucaggca | 1260 |
| cccuuccugu | cagccagccc | aaguccuggg | ccagccucuu | ucaugauucu | aagcccucuu | 1320 |
| ccuccucgcc | gguggccuau | guggaaacua | aguauuccccc | ucccgccaua | ucuccccugg | 1380 |
| uuucugaaaa | gcagguugaa | gucaaagaag | ggccuuguucc | ggucucagag | gauccuguag | 1440 |
| ccauaaagau | ugcagaguug | cuggagaaug | uaacccuaau | ccauaaacca | gugucguugc | 1500 |
| aaccccgugg | gcugaucaau | aaagggaacu | ggugcuacau | uaaugcuaca | cugcaggcau | 1560 |
| ugguugcuug | cccgccgaug | uaccaccuga | ugaaguucau | uccucuguau | uccaaaguagc | 1620 |
| aaaggccuug | uacgucaaca | cccaugauag | acagcuuugu | ucggcuaaug | aaugaguuca | 1680 |
| cuaauaugcc | aguaccuccca | aaaccccgac | aagcucuugg | agauaaaauc | ugagggaua | 1740 |
| uucgcccugg | agcugccuuu | gagcccacau | auauuuacag | acuccugaca | guuaacaagu | 1800 |
| caagccuguc | ugaaaagggu | cgacaagaag | augcugagga | auacuuaggc | uucauucuaa | 1860 |
| auggacuuca | ugaggaaaug | uugaaccuaa | agaagcuucu | cucaccaagu | aaugaaaaac | 1920 |
| uuacgauuuc | caacggcccc | aaaaaccacu | cggucaauga | agaagagcag | gaagaacaag | 1980 |
| gugaaggaag | cgaggaugaa | ugggaacaag | ugggcccccg | gaacaagacu | uccgucaccc | 2040 |
| gccaggcgga | uuuuguucag | acuccaauca | ccggcauuuu | uggugggacac | aucaggcugc | 2100 |
| ugguuuacca | gcagaguuca | aaagaaucug | ccacuuugca | gccauuuuc | acguugcagu | 2160 |
| uggauauccca | gucagacaag | auacgcacag | uccaggaugc | acuggagagc | uugguggcaa | 2220 |
| gagaaucugu | ccaaggguau | accacaaaaa | ccaaacaaga | gguugagaua | agucgaagag | 2280 |
| ugacucugga | aaaacuccccu | ccuguccucg | ugcugcaccu | gaaacgauuc | guuuaugaga | 2340 |

-continued

SEQ ID NO: 1. NCBI Reference Sequence: NM_001272075.1

1

```
agacuggugg gugccagaag cuuaucaaaa auauugaaua uccuguggac uuggaaauua 2400
guaaagaacu gcuuucucca gggguuaaaa auaagaauuu uaaaugccac cgaaccuauc 2460
ggcucuuugc aguggucuac caucacggca acagugcgac gggcggccau uacacuacag 2520
acgucuucca gaucggucug aauggcuggc ugcgcaucga ugaccagaca gucaagguga 2580
ucaaccagua ccaggugguu aaaccaacug cugaacgcac agccuaccuc cuguauuacc 2640
gccgagugga ccugcuguaa acccugugug cgcugugugu gcgcccagug cccgcuucgu 2700
aggacaccac cucacacuca cuucccgccu cucuuuagug gcucuuuaga gagaaacucu 2760
uucucccuuu gcaaaaaugg gcuagaauga aaaggagaug ccuugggguu cgugcacaac 2820
acagcuucug uugacucuaa cuuccaaauc aaaaucauuu gguugaaaca gacuguugcu 2880
ugauuuuaga aaauacacaa aaacccauau uucugaaaua augcugauuc cugagauaag 2940
aaaguggauu ugauccccag ucucauugcu uaguagaaua aauccugcac cagcaacaac 3000
acuuguaaau uugugaaaau gaauuuuauc uuuccuuaaa aaagaaauuu uuuaauccau 3060
cacacuuuuc uucccuaccc uuuaguuuuu gauaaaugau aaaaaugagc caguuaucaa 3120
agaagaacua guucuuacuu caaaagaaaa auaaacauaa aaaauaaguu gcugguuccu 3180
aacaggaaaa auuuuaauaa uuguacugag agaaacugcu uacguacaca uugcagauca 3240
aauauuugga guuaaaaugu uagucuacau agauggguga uuguaacuuu auugccauua 3300
aaagauuuca aauugcauuc augcuucugu guacacauaa ugaaaaaugg gcaaauaaug 3360
aagaucucuc cuucagucug cucuguuuaa uucugcuguc ugcucuucuc uaaugcugcg 3420
ucccuaauug uacacaguuu agugauaucu aggaguauaa aguugcgcc caucaauaaa 3480 aaucacaaag uugguuaaaa aaaaaaaaaa aaaaaaaaaa        3520
```

Following is the Nucleotide Sequence of the siRNAs from Santa Cruz Biotechnology Inc that were Used in the Experiments.

1.
catalog number: sc-76811A:
   Sense: GAAGUUCAUUCCUCUGUAU SEQ ID NO: 2
   Antisense: AUACAGAGGAAUGAACUUC SEQ ID NO: 3
Corresponding cDNA Sequence:
GAAGTTCATTCCTCTGTAT
Nucleotides 1592-1610

2.
catalog number sc-76811B:
   Sense: GAGGAAAUGUUGAACCUAA SEQ ID NO: 4
   Antisense: UUAGGUUCAACAUUUCCUC SEQ ID NO: 5
Corresponding cDNA Sequence:
GAGGAAATGTTGAACCTAA
Nucleotides 1872-1890

3.
catalog number sc-76811C:
   Sense: CCAGUCUCAUUGCUUAGUA SEQ ID NO: 6
   Antisense: UACUAAGCAAUGAGACUGG SEQ ID NO: 7

Corresponding cDNA Sequence:
CCAGTCTCATTGCTTAGTA
Nucleotides 2957-2975

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore to be understood that the appended claims are intended to cover all such modifications and changes as fall within the true spirit of the invention.

The invention claimed is:

1. A method of attenuating expression of USP10 mRNA in an eye of a subject in an area of ocular wound healing, said method comprising: administering to said eye of said subject a composition comprising an effective amount of siRNA directed against USP10 mRNA or a plurality of siRNA directed against USP10 mRNA consisting of a length of 19 to 49 nucleotides and a pharmaceutically acceptable carrier wherein the expression of USP10 mRNA is attenuated resulting in the degradation of one or more αv integrin proteins that are present and which degradation thereby results in inhibiting the persistence of myofibroblasts;

whereby scarring that would result in the absence of application of the siRNA directed against USP10 mRNA or the plurality of siRNA directed against USP10 mRNA is reduced.

2. The method of claim 1 wherein the one or more αv integrin protein is the integrin αvβ5 protein.

3. The method of claim 1 wherein the one or more αv integrin protein is selected from the group consisting of:
the integrin αvβ5 protein, and
one or more of the αv integrin proteins αvβ5, αvβ1 and αvβ3.

4. The method of claim 1 said siRNA directed against USP10 mRNA or plurality of siRNA directed against USP10 mRNA comprising a pool of siRNAs:
5'-GAAGUUCAUUCCUCUGUAUtt-3' SEQ ID NO: 2 (sense nucleotide sequence) and
3'-AUACAGAGGAAUGAACUUCtt-5' SEQ ID NO: 3 (antisense nucleotide sequence),
5'-GAGGAAAUGUUGAACCUAAtt-3' SEQ ID NO: 4 (sense nucleotide sequence) and
3'-UUAGGUUCAACAUUUCCUCtt 5' SEQ ID NO: 5 (antisense nucleotide sequence),
5'-CCAGUCUCAUUGCUUAGUAtt-3' SEQ ID NO: 6 (sense nucleotide sequence) and
3'-UACUAAGCAAUGAGACUGGtt-5' SEQ ID NO: 7 (antisense nucleotide sequence).

5. The method of claim 1, wherein said subject has an ocular scarring or is at risk of developing an ocular scarring as a result of corneal wounds or corneal disease, glaucoma, bleb scarring after trabeculectomy surgery, age-related macular degeneration, diabetic retinopathy, or proliferative vitreoretinopathy.

6. The method of claim 1, wherein said composition is administered via a topical, intravitreal, or transcleral route with a clinically acceptable carrier.

7. A method of eliminating or reducing scarring in an eye of a subject as a result of healing of an ocular wound wherein the healing occurs as fibroblasts differentiate into myofibroblasts that function to close the wound, wherein however, the persistence of myofibroblasts in a wound results in scarring enabled by expression of USP10 mRNA, the method comprising:
administering to the wound a therapeutically effective amount of a siRNA directed against USP10 mRNA to fully or substantially eliminate the expression of USP10 mRNA thereby inhibiting the persistence of myofibroblasts present at the wound healing location.

8. A method as in claim 7 wherein the effect of USP10 in the accumulation of cell surface integrin and subsequent integrin-mediated activation of the fibrotic growth factor TGFβ is reduced and scarring is thereby prevented or reduced.

9. A method for inhibiting scarring of a wound in a mammal comprising: administering a prophylactic or therapeutic amount of a composition to said wound of said mammal, where the composition comprises an effective amount of a siRNA directed against USP10 mRNA or a plurality of siRNA directed against USP10 mRNA consisting of a length of 19 to 49 nucleotides and a pharmaceutically acceptable carrier wherein the expression of USP10 mRNA is attenuated resulting in the degradation of one or more av integrin proteins that are present and which degradation thereby results in inhibiting the persistence of myofibroblasts;
whereby the scarring that would result in the absence of application of the siRNA to USP10 is reduced.

10. The method of claim 9 wherein the αv integrin protein is the integrin αvβ5 protein.

11. The method of claim 9 wherein the αv integrin protein is selected from the group consisting of:
the integrin αvβ5 protein, and one or more of the αv integrin proteins αvβ5, αvβ1 and αvβ3.

12. The method of claim 9 said siRNA directed against USP10 mRNA or plurality of siRNA directed against USP10 mRNA comprising a pool of siRNAs that have a beneficial effect in reducing or preventing scarring:
5'-GAAGUUCAUUCCUCUGUAUtt-3' SEQ ID NO: 2 (sense nucleotide sequence) and
3'-AUACAGAGGAAUGAACUUCtt-5' SEQ ID NO: 3 (antisense nucleotide sequence),
5'-GAGGAAAUGUUGAACCUAAtt-3' SEQ ID NO: 4 (sense nucleotide sequence) and
3'-UUAGGUUCAACAUUUCCUCtt 5' SEQ ID NO: 5 (antisense nucleotide sequence),
5'-CCAGUCUCAUUGCUUAGUAtt-3' SEQ ID NO: 6 (sense nucleotide sequence) and
3'-UACUAAGCAAUGAGACUGGtt-5' SEQ ID NO: 7 (antisense nucleotide sequence).

13. The method of claim 9, wherein said composition is administered via a topical, intravitreal, or transcleral route with a clinically acceptable carrier.

* * * * *

UNITED STATES PATENT AND TRADEMARK OFFICE
CERTIFICATE OF CORRECTION

PATENT NO. : 9,714,424 B1  
APPLICATION NO. : 14/969865  
DATED : July 25, 2017  
INVENTOR(S) : Audrey Bernstein and Stephanie Gilepsie Page 1 of 1

It is certified that error appears in the above-identified patent and that said Letters Patent is hereby corrected as shown below:

In the Specification

Insert the following correction of statement regarding federal sponsored research or development:
--This invention was made with government support under R01EY024942 awarded by the NIH. The government has certain rights in the invention.--

Signed and Sealed this  
Tenth Day of July, 2018

Andrei Iancu  
*Director of the United States Patent and Trademark Office*

SEQUENCE LISTING

<160> NUMBER OF SEQ ID NOS: 19

<210> SEQ ID NO 1
<211> LENGTH: 3520

<212> TYPE: RNA
<213> ORGANISM: Homo sapiens
<300> PUBLICATION INFORMATION:
<308> DATABASE ACCESSION NUMBER: NCBI / NM_001272075.1
<309> DATABASE ENTRY DATE: 2015-09-25
<313> RELEVANT RESIDUES IN SEQ ID NO: (1)..(3520)

<400> SEQUENCE: 1

| | | | | | |
|---|---|---|---|---|---|
| cuccccgcgc | cccgcggcgc | gcggccagug | cgcaggcgcg | gcggccgaug | cgagugugua | 60 |
| ugugcgggcg | agaagauggc | ggcggcgggg | gaagcagcgu | gagcagccgg | aggaucgcgg | 120 |
| agucccaaug | aaacgggcag | ccauggcccu | ccacagcccg | cagcuccugg | gccaugaucc | 180 |
| cauuuucauc | agaugacuug | agaacccaga | agcucuacca | gcacugccau | ucugucccgu | 240 |
| cuugaaacau | caugcccugg | uugcccucuc | cuggaauagg | gcaguauauu | uuuggagauu | 300 |
| uuagcccuga | ugaauucaau | caauucuuug | ugacuccucg | aucuucaguu | gagcuuccuc | 360 |
| cauacagugg | aacaguucug | uguggcacac | aggcugugga | uaaacuaccu | gauggacaag | 420 |
| aauaucagag | aauugaguuu | ggugucgaug | aagucauuga | acccagugac | acuuugccga | 480 |
| gaaccccag | cuacaguauu | ucaagcacac | ugaacccuca | ggcccugaa | uuuauucucg | 540 |
| guuguacagc | uuccaaaaua | accccugaug | uaucacuaa | agaagcaagc | uauggcucca | 600 |
| ucgacugcca | guacccaggc | ucugcccucg | cuuuggaugg | aaguucuaau | guggaggcgg | 660 |
| aaguuuugga | aaaugauggu | gucucaggug | gucuuggaca | aagggagcgu | aaaaagaaga | 720 |
| aaaagcggcc | accuggauau | uacagcuauu | ugaaagaugg | uggcgaugau | aguaucuca | 780 |
| cagaagcccu | ggucaauggc | caugccaauu | cagcaguccc | gaacagguc | agugcagagg | 840 |
| augcagaauu | uauggguugac | augcccccgu | caguuacgcc | caggacuugu | aacagccccc | 900 |
| agaacuccac | agacucuguc | agugacauug | ugccugacag | uccuuucccc | ggagcacucg | 960 |
| gcagugacac | caggacugca | gggcagccag | agggggcgcc | cggggcugau | uugggucagu | 1020 |
| ccugcuuccc | ugcagaggcu | ggcagagaca | cccugucaag | gacagcuggg | gcucagcccu | 1080 |
| gcguuggauc | cgauacuacu | gaaaaccuug | gagugcuaa | uggacaaaua | cuugaauccu | 1140 |
| cgggugaggg | cacagcuacc | aacgggguug | aguugcacac | cacggaaagc | auagacuugg | 1200 |
| acccaaccaa | acccgagagu | gcaucaccuc | cugcugacgg | cacgggcucu | gcaucaggca | 1260 |
| cccuuccugu | cagccagccc | aagucccuggg | ccagccucuu | ucaugauucu | aagcccucuu | 1320 |
| ccuccucgcc | ggugggccuau | uggaaaacua | aguauuccc | uccgccaua | ucccccugg | 1380 |
| uuucugaaaa | gcagguugaa | gucaaagaag | ggcuuguucc | gguuucagag | gauccuguag | 1440 |
| ccauaaagau | ugcagaguug | cuggagaaug | uaacccuaau | ccauaaacca | gugucguugc | 1500 |
| aaccccgugg | gcugaucaau | aaagggaacu | ggugcuacau | uaaugcuaca | cugcaggcau | 1560 |
| ugguugcuu | cccgccgaug | uaccaccuga | ugaaguucau | uccucuguau | uccaaagugc | 1620 |
| aaaggccuug | uacgucaaca | cccaugauag | acagcuuugu | ucggcuaaug | aaugaguuca | 1680 |
| cuaauaugcc | aguaccucca | aaaccccgac | aagcucuugg | agauaaaauc | ugagggaua | 1740 |
| uucgcccugg | agcugccuuu | gagcccacau | auauuuacag | acuccugaca | guuaacaagu | 1800 |
| caagccuguc | ugaaaaggu | cgacaagaag | augcugagga | auacuuaggc | uucauucuaa | 1860 |
| auggacuuca | ugaggaaaug | uugaaccuaa | agaagcuucu | cucaccaagu | aaugaaaaac | 1920 |
| uuacgauuuc | caacggcccc | aaaaaccacu | cggucaauga | agaagagcag | gaagaacaag | 1980 |
| gugaaggaag | cgaggaugaa | ugggaacaag | ugggccccg | aacaagacu | uccgucacccc | 2040 |
| gccaggcgga | uuuuguucag | acuccaauca | ccggcauuuu | uggugacac | aucaggucug | 2100 |

-continued

| | |
|---|---|
| ugguuuacca gcagaguuca aaagaaucug ccacuuugca gccauuuuuc acguugcagu | 2160 |
| uggauaucca gucagacaag auacgcacag uccaggaugc acuggagagc uugguggcaa | 2220 |
| gagaaucugu ccaagguuau accacaaaaa ccaaacaaga gguugagaua agucgaagag | 2280 |
| ugacucugga aaaacuccccu ccuguccucg ugcugcaccu gaaacgauuc guuuaugaga | 2340 |
| agacuggugg gugccagaag cuuaucaaaa auauugaaua uccuguggac uuggaaauua | 2400 |
| guaaagaacu gcuuucucca gggguuaaaa auaagaauuu uaaaugccac cgaaccuauc | 2460 |
| ggcucuuugc aguggucuac caucacggca acagugcgac gggcggccau uacacuacag | 2520 |
| acgucuucca gaucggucug aauggcuggc ugcgcaucga ugaccagaca gucaagguga | 2580 |
| ucaaccagua ccagguggug aaaccaacug cugaacgcac agccuaccuc cuguauuacc | 2640 |
| gccgaguugga ccugcuguaa acccugugug cgcugugugu gcgcccagug cccgcuucgu | 2700 |
| aggacaccac cucacacuca cuucccgccu ucucuuagug gcucuuagaa gagaaacucu | 2760 |
| uucucccuuu gcaaaaaugg gcuagaauga aaaggagaug ccuuggggguu cgugcacaac | 2820 |
| acagcuucug uugacucuaa cuuccaaauc aaaaucauuu gguugaaaca gacuguugcu | 2880 |
| ugauuuuaga aaauacacaa aaacccauau uucugaaaua augcugauuc cugagauaag | 2940 |
| aaagugggauu ugaucccccag ucucauugcu uaguagaaua aauccugcac cagcaacaac | 3000 |
| acuuguaaau uugugaaaau gaauuuuauc uuuccuuaaa aaagaaauuu uuuaauccau | 3060 |
| cacacuuuuc uucccuaccc uuuaguuuuu gauaaaugaa aaaaaugagc caguaucaa | 3120 |
| agaagaacua guucuuacuu caaaagaaaa auaaacauaa aaaauaaguu gcugguuccu | 3180 |
| aacaggaaaa auuuuaauaa uuguacgag agaaacugcu uacguacaca uugcagauca | 3240 |
| aauauuugga guuaaaaugu uagucuacau agaugggguga uuguaacuuu auugccauua | 3300 |
| aaagauuuca aauugcauuc augcuucugu guacacauaa ugaaaauugg gcaaauaaug | 3360 |
| aagaucucuc cuucagucug cucuguuuaa uucugcuguc ugcucuucuc uaaugcugcg | 3420 |
| ucccuaauug uacacaguuu agugauaucu aggaguauaa aguugucgcc caucaauaaa | 3480 |
| aaucacaaag uugguuuaaa aaaaaaaaaa aaaaaaaaaa | 3520 |

<210> SEQ ID NO 2
<211> LENGTH: 19
<212> TYPE: RNA
<213> ORGANISM: Homo sapiens

<400> SEQUENCE: 2
gaaguucauu ccucuguau                                            19

<210> SEQ ID NO 3
<211> LENGTH: 19
<212> TYPE: RNA
<213> ORGANISM: Homo sapiens

<400> SEQUENCE: 3
auacagagga augaacuuc                                            19

<210> SEQ ID NO 4
<211> LENGTH: 19
<212> TYPE: RNA
<213> ORGANISM: Homo sapiens

<400> SEQUENCE: 4
gaggaaaugu ugaaccuaa                                            19

```
<210> SEQ ID NO 5
<211> LENGTH: 19
<212> TYPE: RNA
<213> ORGANISM: Homo sapiens

<400> SEQUENCE: 5
uuagguucaa cauuccuc                                                  19

<210> SEQ ID NO 6
<211> LENGTH: 19
<212> TYPE: RNA
<213> ORGANISM: Homo sapiens

<400> SEQUENCE: 6
ccagucucau ugcuuagua                                                 19

<210> SEQ ID NO 7
<211> LENGTH: 19
<212> TYPE: RNA
<213> ORGANISM: Homo sapiens

<400> SEQUENCE: 7
uacuaagcaa ugagacugg                                                 19

<210> SEQ ID NO 8
<211> LENGTH: 20
<212> TYPE: DNA
<213> ORGANISM: Homo sapiens

<400> SEQUENCE: 8
ctgtccatga aggatgactt                                                20

<210> SEQ ID NO 9
<211> LENGTH: 20
<212> TYPE: DNA
<213> ORGANISM: Homo sapiens

<400> SEQUENCE: 9
tgtccactct gtctgtgaga                                                20

<210> SEQ ID NO 10
<211> LENGTH: 21
<212> TYPE: DNA
<213> ORGANISM: Homo sapiens

<400> SEQUENCE: 10
gtggacagtc ctgccgagta c                                              21

<210> SEQ ID NO 11
<211> LENGTH: 21
<212> TYPE: DNA
<213> ORGANISM: Homo sapiens

<400> SEQUENCE: 11
gagctcccac gagaagaaac a                                              21

<210> SEQ ID NO 12
<211> LENGTH: 20
<212> TYPE: DNA
<213> ORGANISM: Homo sapiens

<400> SEQUENCE: 12
ttgattttgg agggatctcg                                                20
```

```
<210> SEQ ID NO 13
<211> LENGTH: 20
<212> TYPE: DNA
<213> ORGANISM: Homo sapiens

<400> SEQUENCE: 13
gagtcaacgg atttggtcgt                                              20

<210> SEQ ID NO 14
<211> LENGTH: 15
<212> TYPE: DNA
<213> ORGANISM: Homo sapiens

<400> SEQUENCE: 14
tccaagcgga gagag                                                   15

<210> SEQ ID NO 15
<211> LENGTH: 15
<212> TYPE: DNA
<213> ORGANISM: Homo sapiens

<400> SEQUENCE: 15
gtgggtgtga cctga                                                   15

<210> SEQ ID NO 16
<211> LENGTH: 24
<212> TYPE: DNA
<213> ORGANISM: Homo sapiens

<400> SEQUENCE: 16
catctcgttt tcaaagtcca gagc                                         24

<210> SEQ ID NO 17
<211> LENGTH: 21
<212> TYPE: DNA
<213> ORGANISM: Homo sapiens

<400> SEQUENCE: 17
tgagcgtggc tattccttcg t                                            21

<210> SEQ ID NO 18
<211> LENGTH: 20
<212> TYPE: DNA
<213> ORGANISM: Homo sapiens

<400> SEQUENCE: 18
gatcctctga aaccggaaca                                              20

<210> SEQ ID NO 19
<211> LENGTH: 20
<212> TYPE: DNA
<213> ORGANISM: Homo sapiens

<400> SEQUENCE: 19
agagtgcatc acctcctgct                                              20
```